US007198485B2

(12) United States Patent
Hamman

(10) Patent No.: US 7,198,485 B2
(45) Date of Patent: *Apr. 3, 2007

(54) POWDER APPLICATOR FOR TEETH

(76) Inventor: James E. Hamman, 1486 West South Park, Oshkosh, WI (US) 54902

( * ) Notice: Subject to any disclaimer, the term of this patent is extended or adjusted under 35 U.S.C. 154(b) by 0 days.

This patent is subject to a terminal disclaimer.

(21) Appl. No.: 11/184,747

(22) Filed: Jul. 19, 2005

(65) Prior Publication Data

US 2005/0250070 A1 Nov. 10, 2005

Related U.S. Application Data

(63) Continuation-in-part of application No. 10/824,100, filed on Apr. 14, 2004.

(51) Int. Cl.
*A61C 3/02* (2006.01)
(52) U.S. Cl. ..................................... 433/88
(58) Field of Classification Search ............ 433/88, 433/89, 80, 82; 451/90, 91
See application file for complete search history.

(56) References Cited

U.S. PATENT DOCUMENTS

| 2,814,877 | A | 12/1957 | Tilden |
| 3,164,153 | A | 1/1965 | Zorzi |
| 3,971,136 | A | 7/1976 | Madsen |
| 4,522,597 | A | 6/1985 | Gallant |
| 4,741,697 | A | 5/1988 | Herbison |
| 5,120,219 | A | 6/1992 | De Farcy |
| 5,199,229 | A * | 4/1993 | Herold et al. ............. 451/102 |
| 5,286,201 | A | 2/1994 | Yu |
| 5,944,521 | A | 8/1999 | Lawler |
| 6,099,306 | A | 8/2000 | Lawler |
| 6,390,816 | B2 * | 5/2002 | Ito et al. .................. 433/88 |
| 6,416,321 | B2 * | 7/2002 | Gugel et al. .............. 433/88 |
| 6,416,322 | B2 | 7/2002 | Qualliotine et al. |

OTHER PUBLICATIONS

Centrix dental.com, *Accudose Low Viscosity*, product sales web page, www.centrixdental.com (1 page).
PowderPerfekt Instrument, *The Ultimate Support System for Your Cerec*, web page article, www.powderperfekt.com (3 pages).

* cited by examiner

*Primary Examiner*—Melba Bumgarner
(74) *Attorney, Agent, or Firm*—Faegre & Benson LLP

(57) ABSTRACT

The present invention provides an orientation independent apparatus for applying a uniform coating of a dental powder as well as a method of operating the orientation independent apparatus. The present invention can be used in the preparation of a replica tooth during restorative dental work. Included in the present invention is an orientation independent dental powder applicator with a powder reservoir having an introductory circumferential plenum chamber, inner circumferential chamber and outer circumferential plenum chamber. Desiccated pressurized air enters the powder reservoir from a desiccant chamber and fluidizes dental powder located in either the inner circumferential chamber or outer circumferential plenum chamber. The powder reservoir is designed to allow pressurized air to flow around the entire perimeter of either the inner circumferential chamber or outer circumferential plenum chamber. The fluidized dental powder then travels into an acceleration chamber and ultimately through an applicator tube directed at a dental site.

20 Claims, 19 Drawing Sheets

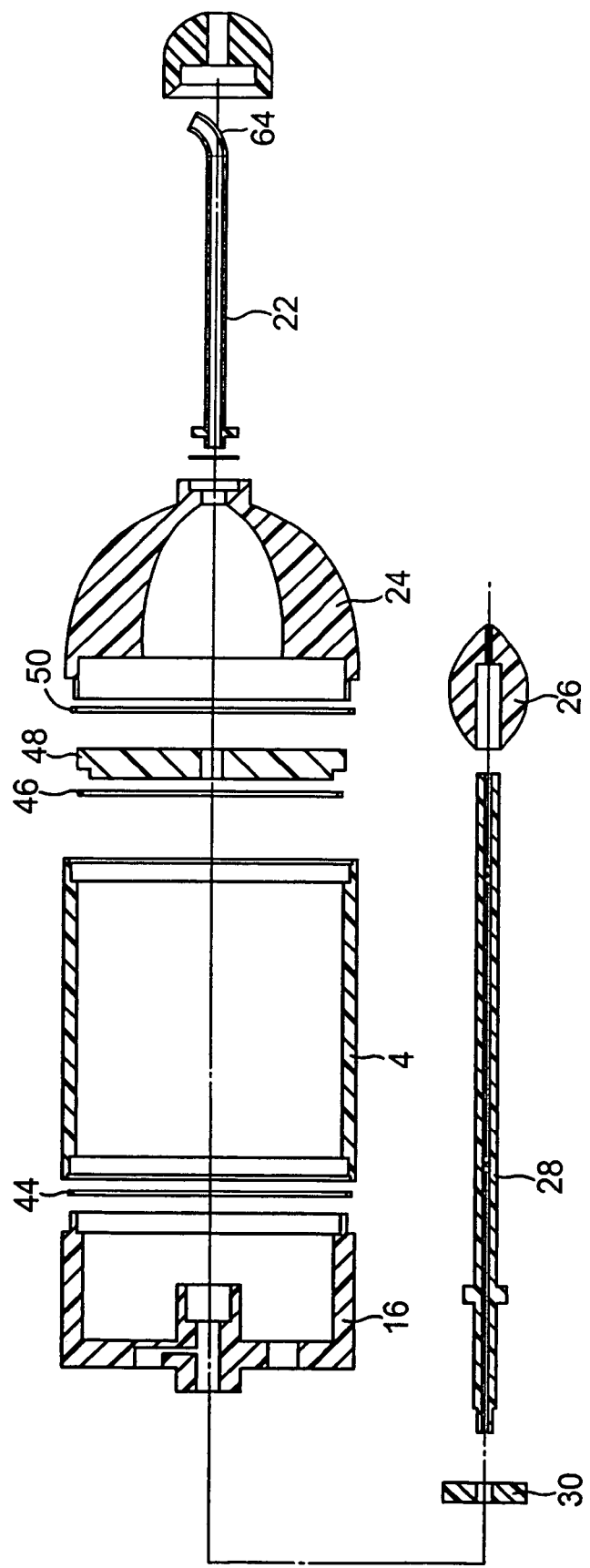

POWDER APPLICATOR FOR TEETH

RELATED APPLICATIONS

This is a continuation in part of U.S. patent application Ser. No. 10/824,100, filed on Apr. 14, 2004, entitled "Powder Applicator for Teeth."

FIELD OF THE INVENTION

The present invention relates to an orientation independent, dental powder applicator and a method of delivering dental powder to a dental site. The present invention can be used, for example, to apply a dental powder such as a contrast medium for imaging of a dental site.

BACKGROUND OF THE INVENTION

Restorative dental work includes making a replica tooth. The replica tooth is made based on the tooth to be restored. A traditional method of creating a replica tooth is to apply a pliable molding material around the tooth to be replaced. The cavity formed in the molding material by the tooth to be replaced can then be used to create a replica tooth of the desired dimensions and shape. More recent dental restoration techniques, however, utilize computer-aided methods.

In order to capture a computer image of the tooth by an imaging device, the tooth is made to contrast with the rest of the patient's mouth by coating the surface of the tooth (also referred to as the dental site) with a suitable powder. This step is known as "powdering" the tooth. Suitable powders include contrast mediums such as titanium dioxide ($TiO_2$).

The contrast medium provides a means by which an infrared camera can photograph and digitize the tooth to be restored. The replica tooth is then designed through the use of a computer. For example, imaging systems such as the system manufactured by Siemens Dental Products Division and distributed in the United States by Patterson Dental Supply, Inc. of St. Paul, Minn. under the name CEREC III include a handheld infrared camera as well as a computer that converts the recorded reflected infrared image of the tooth into values representative of the height and depth of the surface of the tooth. This renders a virtual model of the tooth image that can be utilized to design a virtual restoration for the tooth. Once the design of the replica tooth is completed, the dentist utilizes a milling machine for cutting the actual replica tooth from a ceramic block.

An important tool used with computer-aided dental restoration techniques is a powdering device (also referred to as a dental powder applicator). The powdering device is important because powdering is the first step towards successful completion of restorative dental work. Problems with powdering devices, however, such as clogging, moisture contamination of the imaging powder and limited range of use interfere with the attainment of acceptable results during imaging and digitizing of the dental site. For example, the imaging process requires the application of a uniform coat of powder so that the entire intended dental site is covered. Too much powder is a problem as is too thin a coat. Thus, it is important to have a system and method capable of applying a uniform coat of powder to the dental site.

Existing powdering systems have attempted to overcome these problems with limited success. An early powdering device involved a first container holding pressurized butane gas and the second container holding the contrast medium. The device operated by releasing butane from the first container into the second container. The butane then carried contrast medium out of the second container and through a flexible tube towards the tooth to be coated. Vita Zahnfabrik H. Rauter Graph And Co. KG of Bad Sackingen, Germany distributed such an applicator. Alternative suppliers of the butane propellant devices included IVOCLAR (sold as ProCad powder) and VITA brand contrast medium.

Existing powdering systems, including the butane propellant device, require additional preparation steps such as applying imaging liquid with a brush to all the surfaces visible in the imaging step and blow drying these surfaces after application of the imaging liquid. Following these preparation steps, the dental powder was sprayed on in a steady stream from a nozzle held about one or two centimeters from the tooth surface. Difficulties were encountered with the butane propellant device, however, when trying to achieve uniform and even application of the powder in remote locations of the mouth. For instance, in many cases the patient's cheek is in the proximity of the side of the tooth and thus must be forced outwardly therefrom in order for the powder to be sprayed evenly on the side of the tooth. Because the butane propellant device uses an outlet stem that bends when contacted against the cheek, the user of the device had to force the cheek away using a second hand or additional device, which added further complexity to the powdering process.

An alternative device is described in U.S. Pat. Nos. 5,944,521 and 6,099,306 entitled Tooth Powdering Applicator (the Lawler device). The Lawler device replaces the attached container of pressurized butane with a connection to a pressurized fluid. The outlet tube is rigid and curved. The Lawler device allows a dentist to use a single hand to hold the device and simultaneously rotate the outlet tube without use of the dentist's second hand. The stated advantage of the Lawler device was that the outlet tube could be rotated to allow the discharge stream from the powdering device to be aimed at various tooth surfaces without having to tilt the powder reservoir. Tilting the powder reservoir in the powdering device, however, leads to sporadic powder flow, clumping of the powder and ultimately clogging of the powdering device. A device based on the Lawler patent is sold under the name POWDERMEISTER by Powder Meister, Inc. of Bloomington, Ind.

Despite the purported advantages of the Lawler device, the powder reservoir of the POWDERMEISTER device must still be held in an upright or vertical position to allow the powder to enter the airstream. Some powder clumps are also attributed to storing the POWDERMEISTER on its side or upside down so that excess powder enters the powdering tube. Water in the pressurized source of air poses a further problem with the POWDERMEISTER as the water will cause the powder to clump. An additional problem with the POWDERMEISTER device is introduced by a thumbscrew controlled air valve on the container. The amount of powder applied to the tooth is very sensitive to the position of the thumbscrew. That is, very little movement of the thumbscrew is needed to effect a change in the powder flow. Some dentists find that thumbscrews turn too freely.

Another alternative powdering device is disclosed in U.S. Pat. No. 6,416,322 to Qualliotine et al. (the Quallitone patent). A device based on the Quallitone patent is sold under the name POWDERPERFEKT by Ourglass Ltd. of Greenville, N.C. The POWDERPERFEKT device states several objects including providing a device that eliminates powder clumping caused by moisture in the pressurized air supply. Despite this, the POWDERPERFEKT design is still prone to clogging for several reasons.

First, there is a 90-degree bend that the fluidized contrast medium must take prior to exiting the apparatus. The velocity of the contrast medium impacts upon the 90-degree bend causing a deposition of powder that blocks the air passage. This is also true of the butane propellant device and the POWDERMEISTER device.

Second, the POWDERPERFEKT device depends upon the pressurized air line to be dry between the air compressor and desiccant only and does not address the need for keeping the powder dry between uses or ensuring that the air supply is dry prior to contact with the dental powder.

Third, as with the butane propellant device and the POWDERMEISTER device, the powder container must have a sufficient level of dental powder to ensure that the dental powder is sufficiently fluidized. This is because the design of the POWDERPERFEKT device directs the path of air down into the powder where it disperses and aerolizes the dental powder inefficiently by causing large drifts of the dental powder to form necessitating physical agitation or tapping of the powder container to keep the powder in the path of the air stream. The powder then must travel up into the 90-degree bend turn prior to exiting the device. There is also a large discrepancy between the volume of gas and fluidized material in the powder container and the small orifice that it exits. This discrepancy leads to an abrupt change in velocity of the powder stream resulting in clogging. Finally, there are limitations respecting angles that the disclosed device can be tilted during use before the dental powder jams. The same is true for the POWDERMEISTER device.

Fourth, the intrinsic nature of the air control button to initiate the powder flow is too course to allow sufficient fine control of the airflow. Thus, the air pressure flowing through the powder chamber is high and not adjustable, which leads to excessive powder application.

BRIEF SUMMARY OF THE INVENTION

The present invention provides an orientation independent apparatus for applying a uniform coating of a dental powder. The present invention also includes a method of delivering dental powder to a dental site. The present invention can be used in the preparation of a replica tooth during restorative dental work.

In one embodiment of the present invention, the apparatus includes an orientation independent dental powder applicator (also referred to as a dental powder applicator) that includes a powder reservoir having an inner porous wall extending around a longitudinal axis and surrounding an inner circumferential chamber as well as an outer porous wall extending around the inner porous wall. The dental powder applicator also includes an outer circumferential plenum chamber extending around the longitudinal axis and substantially surrounding the inner porous wall as well as an introductory circumferential plenum chamber extending around the longitudinal axis and substantially surrounding the outer circumferential plenum chamber. A membrane can be located within the introductory circumferential plenum chamber such that it also extends around the longitudinal axis and substantially surrounds the outer circumferential plenum chamber. A dental powder is located in the outer circumferential plenum chamber. The dental powder applicator further includes a desiccant chamber containing a desiccant material. The desiccant chamber has a first end with an air input opening and a second end fluidly coupled to the introductory circumferential plenum chamber. An applicator tube is fluidly coupled at a proximal end to an inner circumferential chamber. A distal end of the applicator tube is adapted to deliver the dental powder to a dental site.

In another embodiment of the present invention, the apparatus includes an orientation independent dental powder applicator that includes a powder reservoir having an introductory circumferential plenum chamber substantially surrounded by an inner circumferential plenum chamber that extends around a longitudinal axis. This embodiment can further include a membrane located within the introductory circumferential plenum chamber and that extends around the longitudinal axis and to substantially surround the introductory circumferential plenum chamber. The membrane is located between the introductory circumferential plenum chamber and an inner porous wall. The inner porous wall extends around the longitudinal axis and is substantially surrounded by inner circumferential chamber, which also extends around a longitudinal axis. In this embodiment is further included an outer porous wall extending around the inner porous wall and substantially surrounding the inner circumferential chamber. The dental powder applicator also includes an outer circumferential plenum chamber extending around the longitudinal axis and substantially surrounding the outer porous wall. An outer wall surrounds the outer circumferential plenum chamber. A dental powder is located in the inner circumferential chamber. The dental powder applicator further includes a desiccant chamber containing a desiccant material. The desiccant chamber has a first end with an air input opening and a second end fluidly coupled to the inner circumferential chamber. An applicator tube is fluidly coupled at a proximal end to the outer circumferential plenum chamber. A distal end of the applicator tube is adapted to deliver the dental powder to a dental site.

In yet another embodiment of the present invention is a method of delivering dental powder to a dental site. Delivery of the dental powder includes the steps of introducing pressurized air into a desiccant chamber of an orientation independent dental powder applicator through a first air input opening and desiccating the pressurized air. The method further includes the steps of directing the desiccated pressurized air into a powder reservoir and then circumferentially fluidizing the dental powder contained in the powder reservoir with the desiccated pressurized air. The fluidized dental powder and desiccated pressurized air is then directed towards an applicator tube along a longitudinal axis of the orientation independent dental powder applicator. The fluidized dental powder and desiccated pressurized air is additionally directed through the applicator tube, the applicator tube having a distal end directed towards the dental site facilitating application of the dental powder on the dental site.

BRIEF DESCRIPTION OF THE SEVERAL VIEWS OF THE DRAWING

With reference to the attached Figures, it is to be understood that like components are labeled with like numerals throughout the several Figures.

FIG. 1 is a schematic illustration in cross section parallel to the longitudinal axis of a dental powder applicator having an inner circumferential chamber to receive fluidized dental powder in accordance with the present invention.

FIG. 2 is a schematic illustration in cross section parallel to the longitudinal axis of a dental powder applicator having an inner circumferential chamber to receive fluidized dental powder showing the direction of air flow through the dental powder applicator in accordance with the present invention.

FIG. 12 is a schematic illustration of a cross sectional view of a dental powder applicator showing the arrangement of the component parts in accordance with the present invention.

FIG. 13 is a schematic view of a cylindrical inner porous wall in accordance with the present invention.

FIG. 14 is a schematic view of a conical inner porous wall in accordance with the present invention.

DETAILED DESCRIPTION OF THE INVENTION

The present invention provides an orientation independent apparatus for applying a uniform coating of a dental powder. In one embodiment of the present invention, orientation independent refers to the ability to position the longitudinal axis of the apparatus at any angle relative to a dental site.

The present invention is also related to a method of operating the orientation independent apparatus. The present invention can be used in the preparation of a replica tooth during restorative dental work. In particular, the present invention can be used to provide a uniform, very thin coating of consistent thickness of a contrast medium, such as a reflective powder like titanium dioxide ($TiO_2$) or other suitable dental powder or imaging medium, to an area to be scanned by an infrared laser camera system or other such scanning devices such as the dental CAD/CAM restoration design and fabrication equipment in the Seimens (Sirona) CEREC machine series I, II, and III.

Figure 1:
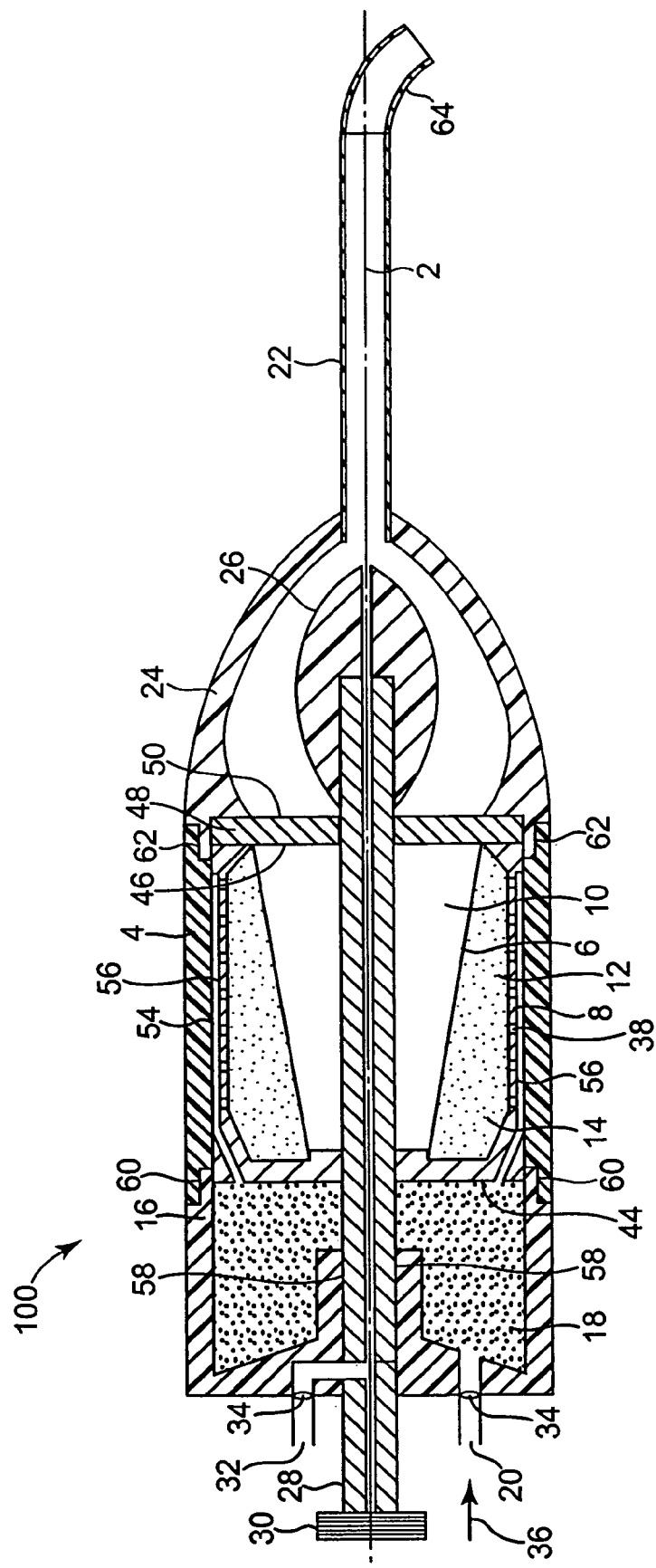

The apparatus and method of the present invention will be described in part with reference to FIGS. 1 to 21. FIG. 1 is a schematic illustration of one embodiment of an orientation independent, dental powder applicator 100 (also referred to as a dental powder applicator) in accordance with the present invention. The dental powder applicator 100 of FIG. 1 includes a powder reservoir 4 extending around a longitudinal axis 2 of the powder reservoir. The inner porous wall 6 therefore surrounds an inner circumferential chamber 10 of the powder reservoir 4. In one embodiment of the present invention, the inner circumferential chamber 10 is the shape of a circle but the term circumferential is also defined as the external boundary or surface of a figure or object. Therefore, the term circumferential is not intended to be restricted to only circles and other shapes are also contemplated by the invention.

Figure 9:
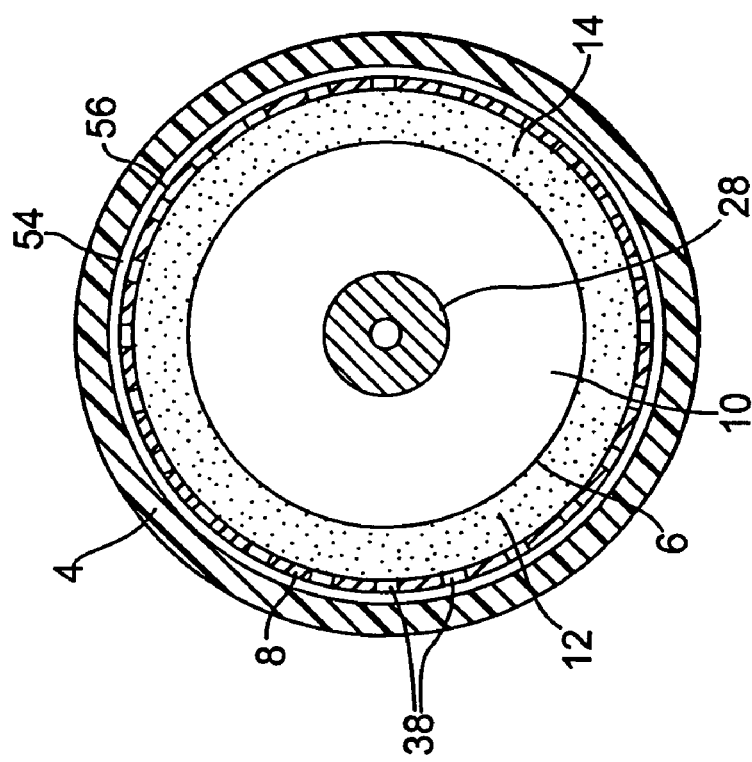
FIG. 9 is a schematic illustration of a cross sectional view perpendicular to the longitudinal axis of a powder reservoir having an inner circumferential chamber to receive fluidized dental powder in accordance with the present invention.

The powder reservoir 4 further includes an outer porous wall 8 extending around and substantially surrounding the inner porous wall 6. The area located between the outer porous wall 8 and the inner porous wall 6 is an outer circumferential plenum chamber 12. The outer circumferential plenum chamber 12 extends around the longitudinal axis 2 of at least the outer porous wall 8. The powder reservoir also includes an introductory circumferential plenum chamber 54 extending around the longitudinal axis and substantially surrounding the outer porous wall 8. A membrane 56 can be located within the introductory circumferential plenum chamber 54 such that the membrane 56 also extends around the longitudinal axis and substantially surrounds the outer circumferential plenum chamber 12. In this embodiment of the present invention, dental powder 14 is located in the outer circumferential plenum chamber 12. FIG. 9 is a schematic illustration of a cross sectional view perpendicular to the longitudinal axis 2 of a powder reservoir 4 in accordance with the present invention having an inner circumferential chamber to receive fluidized dental powder.

Figure 15:
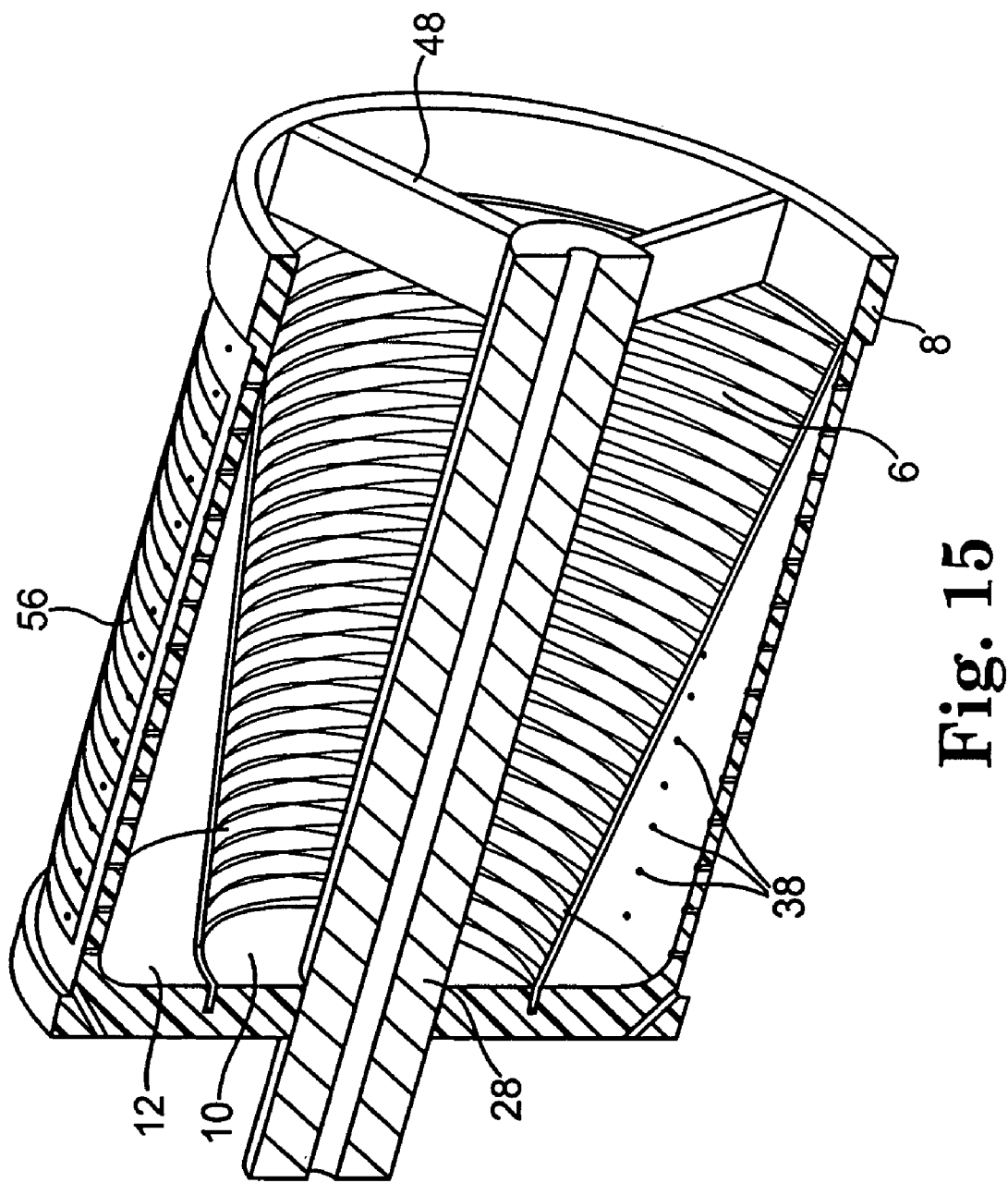
FIG. 15 is a detailed schematic view of components contained within a powder reservoir in accordance with the present invention.
Figure 16C:
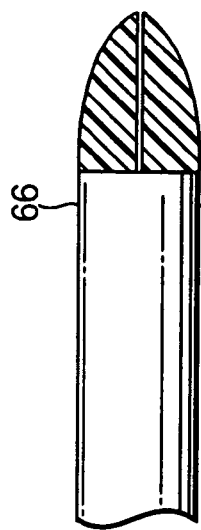
FIGS. 16A, 16B, 16C and 16D are schematic illustrations showing different airfoil shapes in accordance with the present invention.
Figure 16D:
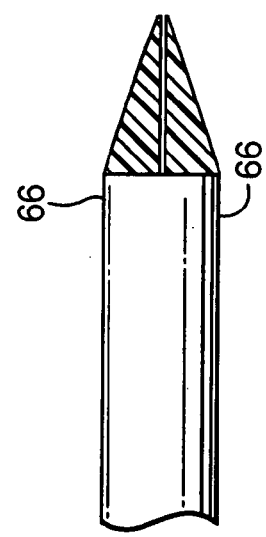
Figure 16A:
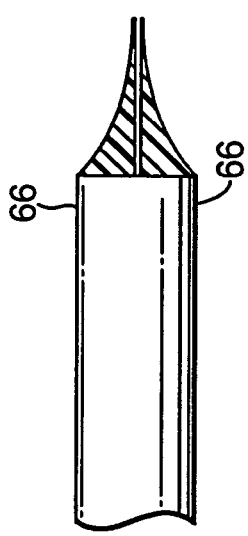
Figure 16B:
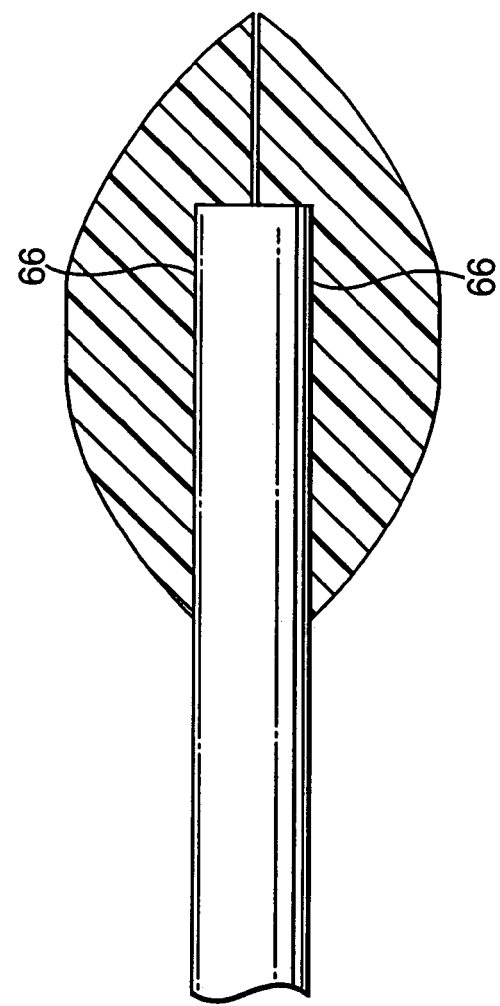

FIG. 15 illustrates in greater detail the components of the powder reservoir previously described. In particular, FIG. 15 illustrates the outer porous wall 8 as well as the membrane 56 that extends around the outer porous wall 8. FIG. 15 further illustrates the inner porous wall 6 and the placement of the control rod 28 within an end cap 48. FIG. 15 also includes the openings 38 in the outer porous wall 8 of the present invention. In one embodiment, the openings 38 are generally cylindrical holes but other shapes that promote uniform and sufficient airflow are also contemplated by the present invention and are within the knowledge of one skilled in the art. In one embodiment of the present invention the openings 38 have a maximum cross-sectional dimension of from about 50 microns to about 1-millimeter. The openings 38 can be positioned in either a regular or irregular pattern in the outer porous wall 8 such that the openings 38 direct desiccated pressurized air into the outer circumferential plenum chamber 12 to substantially fluidize the dental powder in a random pattern. The openings 38 are preferably located around the entire perimeter of the outer porous wall 8 so that the desiccated pressurized air enters the outer circumferential plenum chamber 12 in a substantially 360-degree pattern. As a result, the dental powder applicator 100 can be oriented, tipped, held, rotated and the like in any direction and the dental powder 14 contained within the outer circumferential plenum chamber 12 will still be agitated by the desiccated pressurized air and directed generally towards the longitudinal axis 2 of the powder reservoir 4.

Further included in an embodiment of the present invention is a desiccant chamber 16 containing a desiccant material 18. In one embodiment of the present invention the desiccant chamber 16 can be joined to the powder reservoir 4 at a first coupling 60 by threads, sliding, pushing, snap connections, interference fits, spring connections and the like. The desiccant chamber 16 of the present invention includes a first air input opening 20 and a second air input opening 32 at a first end. In this embodiment of the present invention, the desiccant chamber 16 is fluidly coupled at a second end to the introductory circumferential plenum chamber 54 of the powder reservoir 4. A schematic illustration of a cross sectional view perpendicular to the longitudinal axis 2 of the desiccant chamber in accordance with the present invention is provided as FIG. 8.

In one embodiment of the present invention, the dental powder applicator 100 is further connected to a pressurized air source at a first air input opening 20 and a second air input opening 32 at a first end of the desiccant chamber 16. The pressurized air source 36 can be, for example, compressed air or other suitable gasses such as nitrogen, helium, argon, or similar inert gases. The pressurized air source is directed into two distinct paths through one-way valves 34 that ensure unidirectional flow of the pressurized air. In one embodiment of the present invention, pressurized air entering the first air input opening 20 is controlled with a variable flow switch that can be operated manually, such as a foot pedal. The pressurized air entering the second air input opening can be controlled by an on/off switch, such as a push button actuator or a variable fine control needle valve.

Pressurized air entering the first air input opening 20 is directed through the desiccant chamber 16 where it contacts the desiccant material 18. The desiccant material 18 located within the desiccant chamber 16 assists removal of moisture from the pressurized air, thus providing a source of desiccated pressurized air that can be used to fluidize, agitate and propel the dental powder. The removal of moisture reduces the potential for clumping of the dental powder. Pressurized air entering the second air input opening 32 is directed into a sealed chamber, prior to and separate from the desiccant chamber, and further flows from the sealed chamber into an interior portion of a control rod 28.

The desiccated pressurized air (also referred to as desiccated air) is directed from the desiccant chamber 16 into the powder reservoir 4. In one embodiment, the desiccated pressurized air travels from the desiccant chamber 16 to an introductory circumferential plenum chamber 54 and then through a plurality of openings 38 located in the outer porous wall 8. In one embodiment of the present invention is further included a membrane 56 located within the introductory circumferential plenum chamber 54 to reduce backflow of dental powder 14 from the powder reservoir 4 to the desiccant chamber 16.

The inner porous wall 6 separates the outer circumferential plenum chamber 12 from the inner circumferential chamber 10. The inner porous wall 6 of the present invention also includes openings 40. In one embodiment of the present invention the openings 40 of the inner porous wall 6 have a maximum cross-sectional dimension of from about 50 microns to about 1-millimeter. In one embodiment of the present invention, the inner porous wall 6 can include one or more of a mesh screen, a membrane, a filter media, a perforated sheet material, synthetic woven material or like material. Thus, in one embodiment of the present invention, the inner porous wall 6 also filters particles of dental powder 14 that exceed the maximum cross-sectional dimension of the openings. The dimensions of the inner porous wall 6 can also include a length measured in the direction of the longitudinal axis 2 that is from at least about two to about 10 times greater than a maximum gap between the inner porous wall 6 and the outer porous wall 8. Thus, the present invention also provides uniform velocity of pressurized air along the entire length of the inner porous wall 6 as well as large as possible of an area for the fluidized particles to be filtered through prior to passing to and through the powder reservoir 4 and ultimately an acceleration chamber 24.

The present arrangement further promotes, for example, a direct linear path of the fluidized dental powder 14 through the inner porous wall 6 to the inner circumferential chamber 10 as well as sufficient surface area on the inner porous wall 6. The shape of the inner porous wall 6 can include, for example, a cylinder, a cone, or a continuously curved surface. FIG. 13 illustrates a schematic view of a cylindrical inner porous wall 6 in accordance with the present invention and FIG. 14 illustrates a schematic view of a conical inner porous wall 6 in accordance with the present invention.

The present invention further includes an applicator tube 22 having a proximal end fluidly coupled to the inner circumferential chamber 10 of the powder reservoir 4 and a distal end adapted to deliver the dental powder 14 to a dental site. In one embodiment of the present invention a tip 64 can be joined to the distal end of the applicator tube 22. In one embodiment of the present invention the tip 64 is releasably attached. The tip 64 can also be adapted to deliver the dental powder 14 to a dental site. The tip 64 can be disposable or reusable. An example of a tip 64 is a disposable tip such as a Centrix ACCUDOSE high viscosity tube, (available from Centrix Dental, Shelton, Conn.). In one embodiment of the present invention the applicator tube 22 is releasably attached to the dental powder applicator 100. In yet another embodiment, the applicator tube 22 is rotatably attached to the dental powder applicator 100. In one embodiment of the present invention, the applicator tube 22 is constructed of a rigid material that permits the user to displace objects, such as the cheek of a patient receiving dental treatment, by pressing the applicator tube 22 against the object.

Located generally between the powder reservoir 4 and the applicator tube 22 is an acceleration chamber 24. In one embodiment of the present invention, the powder reservoir 4 can be joined to the acceleration chamber 24 a second coupling 62 by threads, sliding, pushing, snap connections, interference fits, spring connections and the like.

Figure 6:
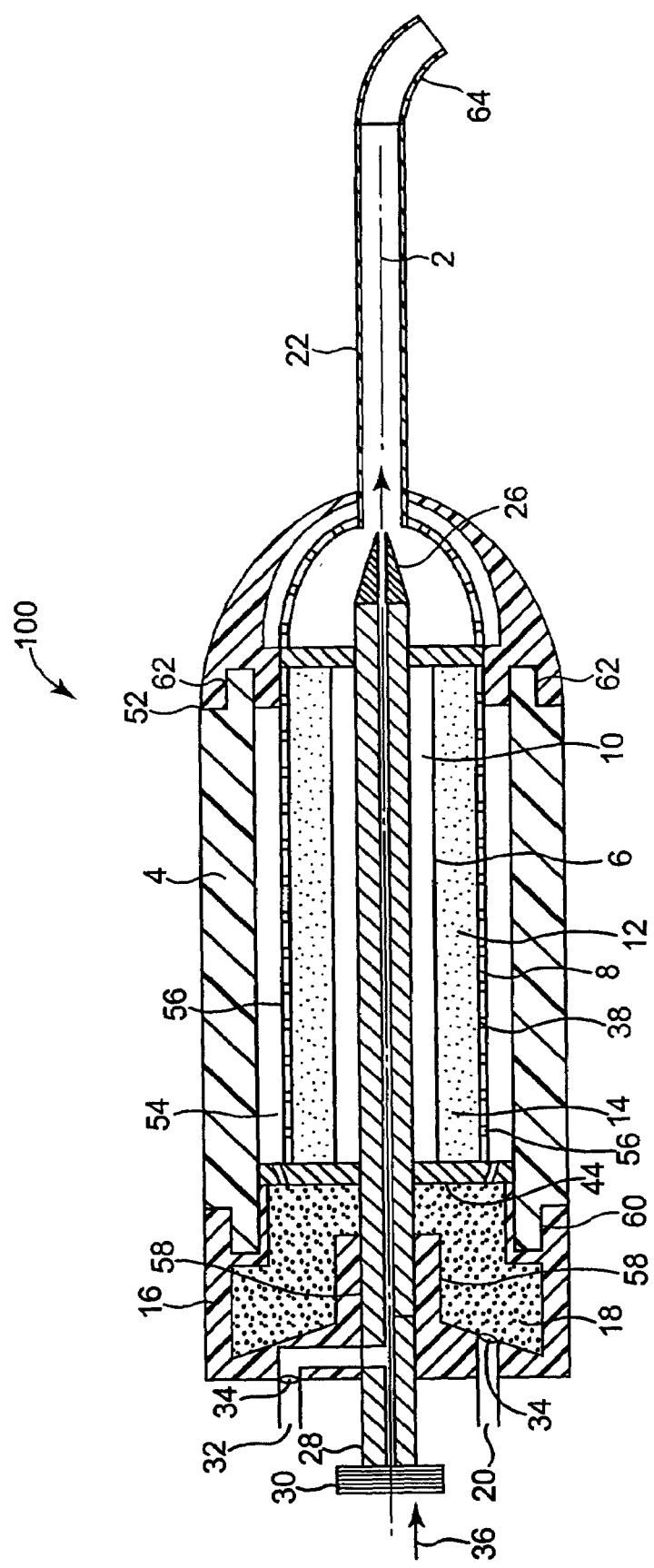
FIG. 6 is a schematic illustration of a cross section parallel to the longitudinal axis of a dental powder applicator having an inner circumferential chamber to receive fluidized dental powder showing a powder chamber and an acceleration chamber as a combined assembly in accordance with the present invention.
Figure 11:
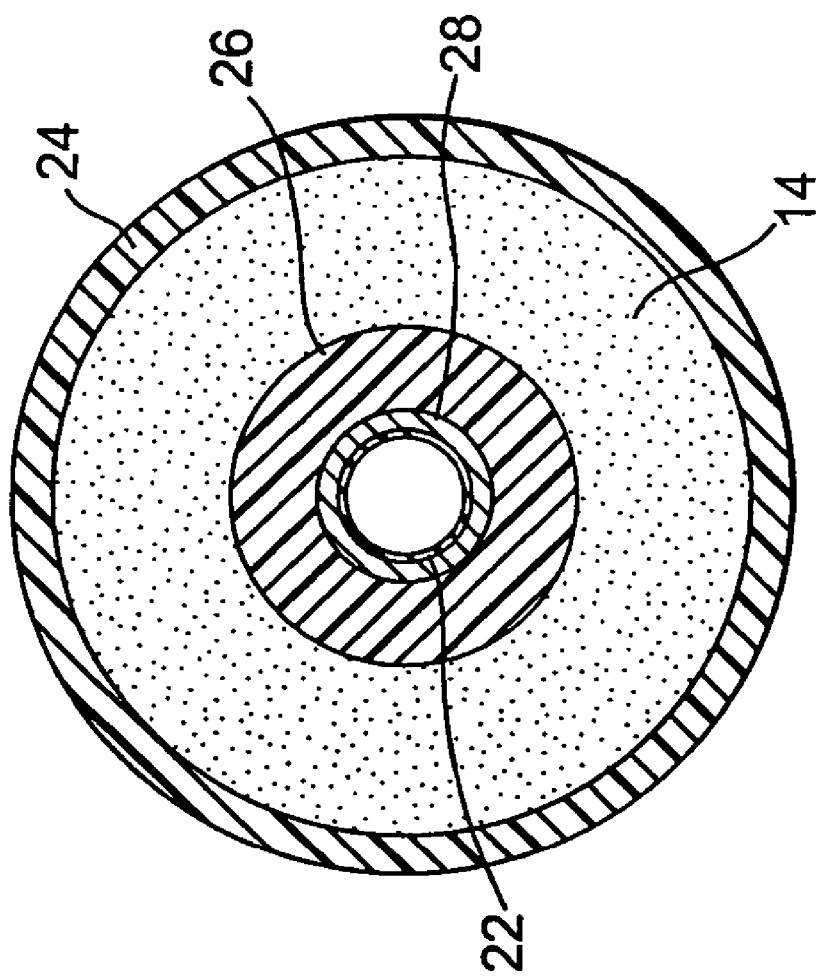
FIG. 11 is a schematic illustration of a cross sectional view perpendicular to the longitudinal axis of an acceleration chamber in accordance with the present invention.
Figure 18A:
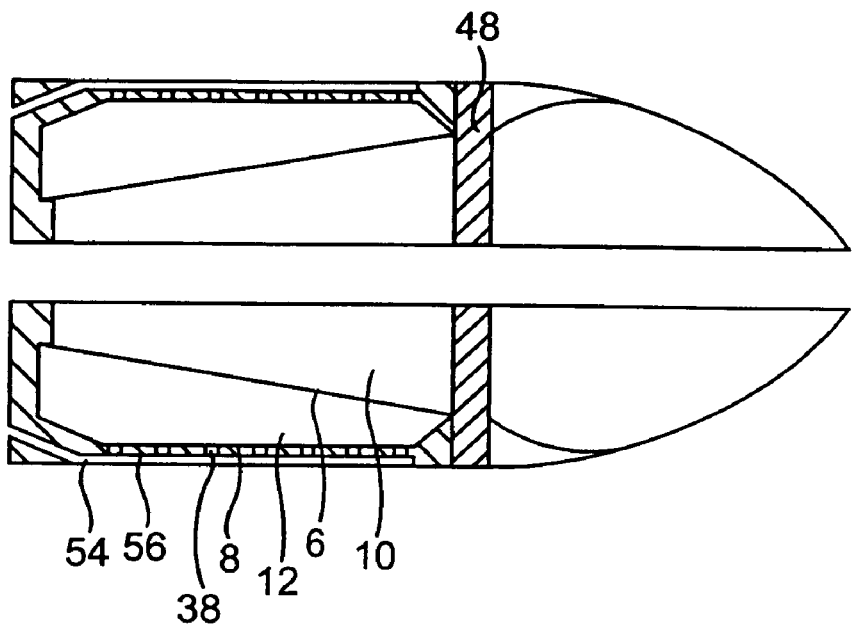
FIGS. 18A and 18B are schematic illustrations in cross-section parallel to the longitudinal axis of a removable cartridge of a dental powder applicator in accordance with the present invention.
Figure 18B:
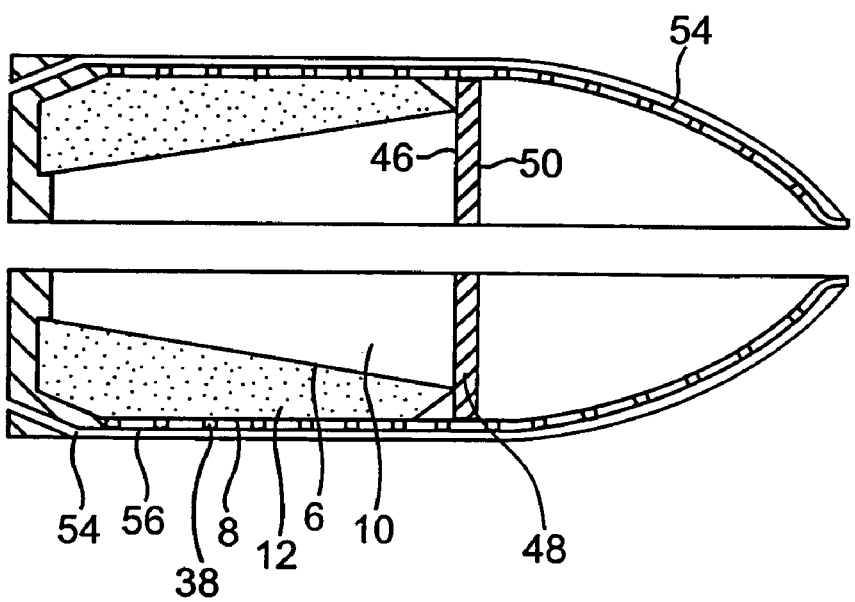
Figure 21:
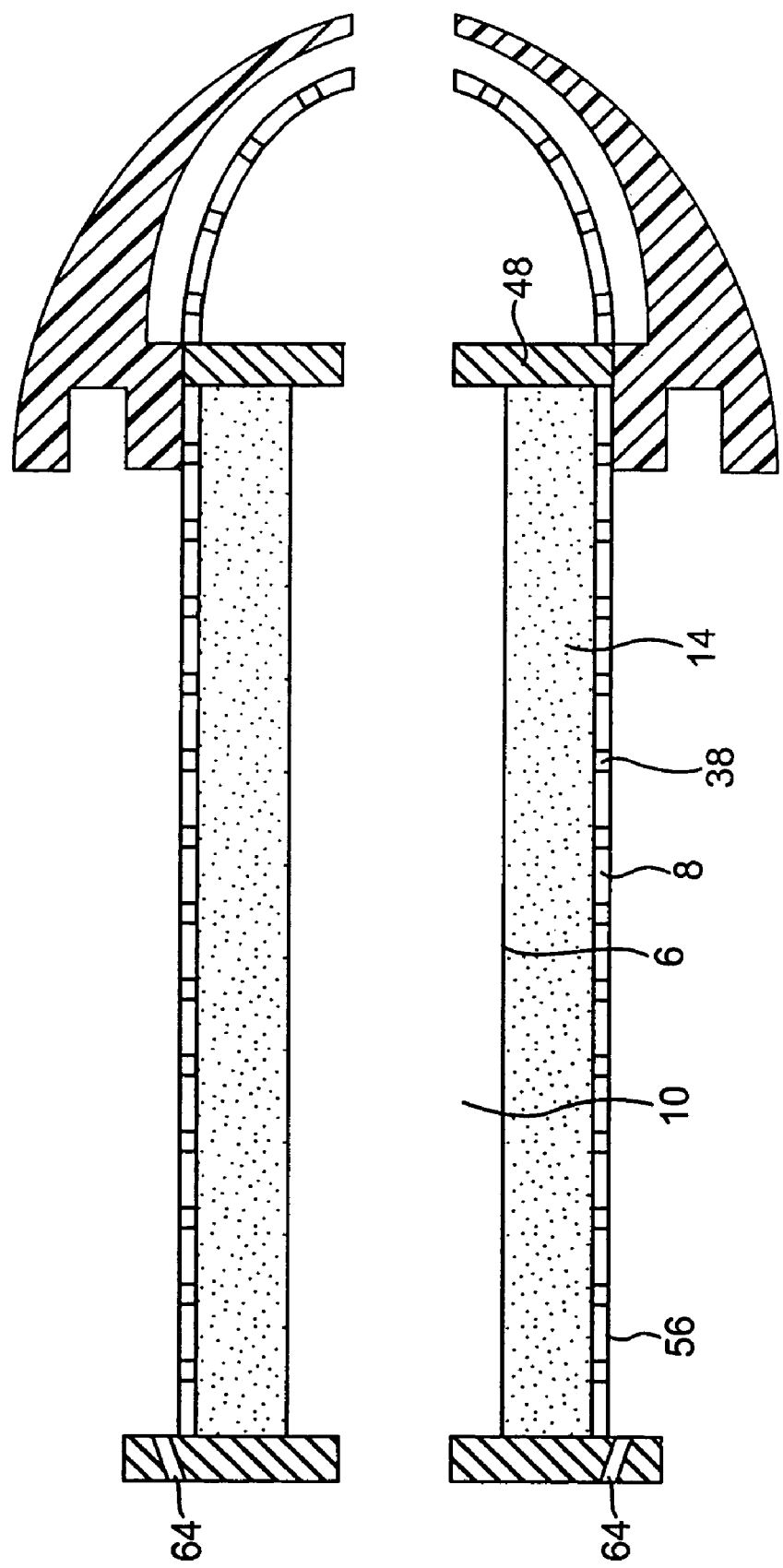
FIG. 21 is a schematic illustration in cross section parallel to the longitudinal axis of a removable cartridge of a dental powder applicator in accordance with the present invention.

A cross sectional view of the acceleration chamber perpendicular to the longitudinal axis of the dental powder applicator in accordance with the present invention is provided in FIG. 11. In one embodiment of the present invention, the acceleration chamber 24 is fluidly coupled between the inner circumferential chamber 10 of the powder reservoir 4 and the applicator tube 22. In an alternative embodiment, as illustrated in FIG. 6, the inner circumferential chamber 10 and acceleration chamber 24 are assembled as one piece. In this embodiment, the combined inner circumferential chamber 10 and acceleration chamber 24 can be inserted as a cartridge into the powder reservoir 4 and contact the desiccant chamber 16. The cartridge can be pre-loaded with dental powder 14 and pressurized with a gas such as nitrogen to prevent ambient moisture in air from contaminating the dental powder 14 during periods of non-use. Alternatively, the components substantially surrounded by the introductory plenum chamber 54 of the powder reservoir 4 can be inserted as a cartridge that is either refillable or reloadable. In one embodiment of the present invention, the cartridge is releasably attached to the desiccant chamber 16. In yet another embodiment of the present invention, the cartridge is releasably attached to both the desiccant chamber 16 and the acceleration chamber 24. FIGS. 18A, 18B and 21 illustrate refillable or reloadable cartridges in accordance with the present invention.

Figure 19:
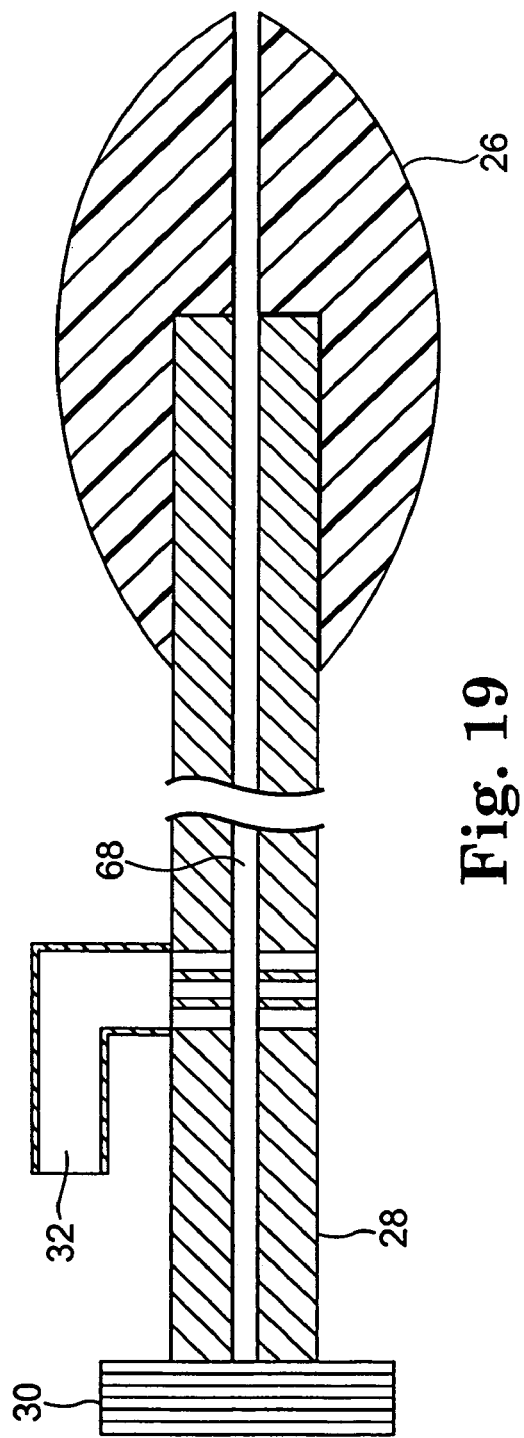
FIG. 19 is a schematic illustration in cross section parallel to the longitudinal axis of a control rod and airfoil in accordance with the present invention.
Figure 20:
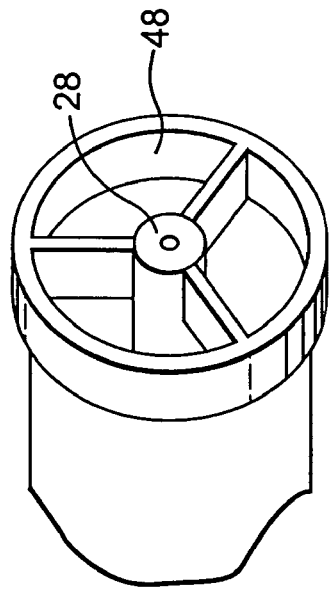
FIG. 20 is a schematic illustration of an end cap in accordance with the present invention.

The acceleration chamber 24 includes an airfoil 26 coupled to the control rod 28 as is illustrated by FIG. 19. As is illustrated in FIGS. 16A–16D, in one embodiment of the present invention, the control rod 28 can be joined to the airfoil 26 at a third coupling 66 by threads, sliding, pushing, snap connections, interference fits, spring connections and the like. The fluidized dental powder 14 travels past the airfoil 26 to reach the distal end of the applicator tube 22. The airfoil 26 not only ensures a direct and straight path of flow for the fluidized dental powder 14 but the shape and dimensions of the airfoil 26 also provide gradual acceleration of the fluidized dental powder 14 towards the proximal end of the applicator tube 22 with minimal disturbance or obstruction.

As illustrated in FIGS. 16A–16D, suitable shapes for the airfoil 26 include fusiform, conical, tapered, and symmetrical shapes. The airfoil 26 is further connected to the control rod 28, which is adapted to, in part, displace the airfoil 26 within the acceleration chamber 24. More specifically, the control rod 28 includes a control rod actuator 30 to adjust the longitudinal position of the control rod 28, and ultimately the air foil 26, which affects the exit diameter of the opening to the proximal end of the applicator tube 22. Therefore, it is possible to regulate the volume and velocity of the fluidized dental powder 14 traveling through the acceleration chamber 24 and into the applicator tube 22. The airfoil 26 can also be displaced into a sealing engagement with the proximal end of the applicator tube 22, which can prevent ambient moisture in air from contaminating the dental powder 14 during periods of non-use. In one embodiment of the present invention, the control rod threaded 56 and is displaced by rotating the control rod actuator 30. Alternative methods of adjusting the longitudinal position of the control rod are also contemplated by the present invention however, such as by pushing and sliding the control rod in the longitudinal direction.

In another embodiment of the present invention, pressurized air entering the second air input opening 32 and flowing through the interior portion 68 of a control rod 28 can be used as supplemental pressurized air to further regulate the volume and velocity of the fluidized dental powder 14. The supplemental pressurized air can also provide a purging source or additional velocity of dental powder 14 free air to be directed through the applicator tube 22.

Figure 3:
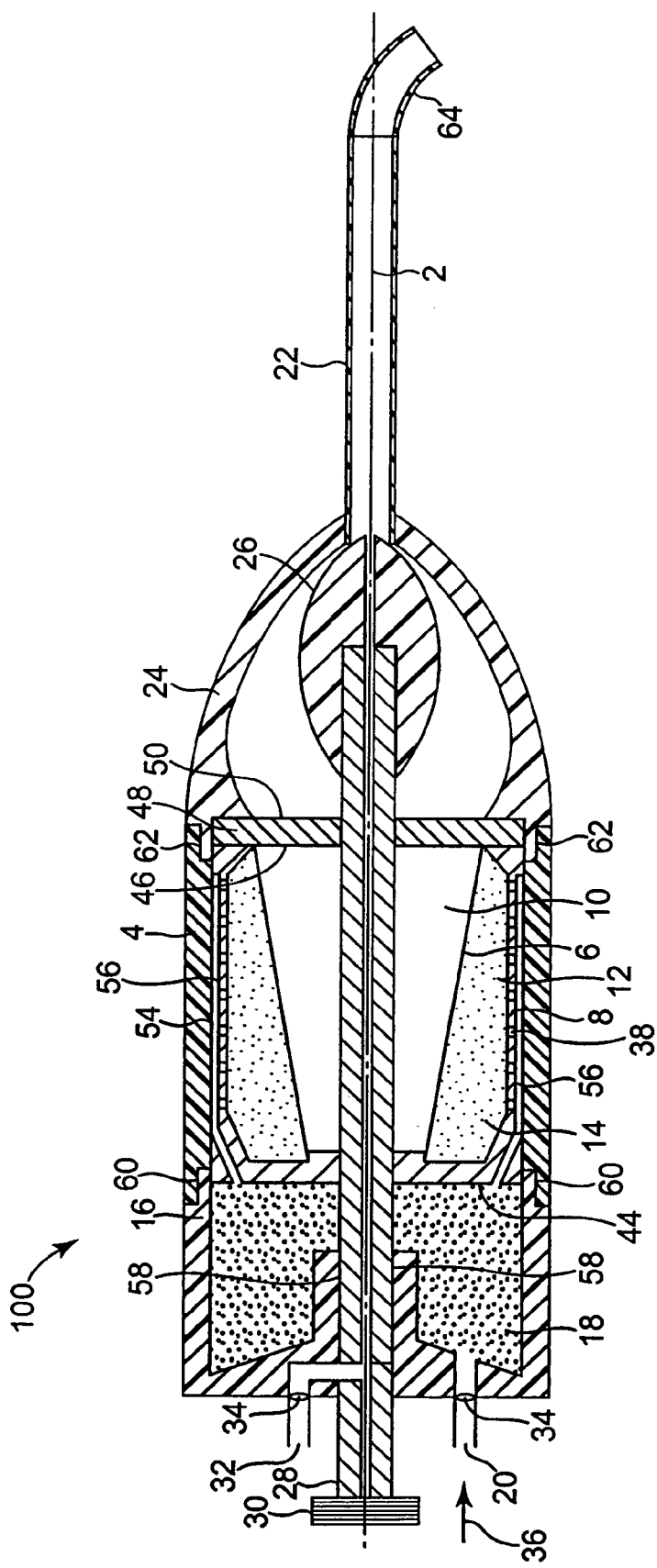
FIG. 3 is a schematic illustration in cross section parallel to the longitudinal axis of a dental powder applicator having an inner circumferential chamber to receive fluidized dental powder showing an airfoil engaged with an applicator tube in accordance with the present invention.

The control rod 28 of the present invention traverses the longitudinal axis 2 of the dental powder applicator 100 with the proximal end of the control rod 28 located at or near the first end of the desiccant chamber 16 and the distal end of the control rod 28 located within the acceleration chamber 24. As such, the control rod 28 extends through the desiccant chamber 16 and powder reservoir 4 and into an acceleration chamber 24. In one embodiment of the present invention, the control rod 28 extends out of the first end of the desiccant chamber 16. The control rod 28 is attached at a first or proximal end to the control rod actuator 30, which is further attached at a second or distal end to the airfoil 26. In one embodiment of the present invention, the control rod actuator 30 can be a knob, gripping device, handle or the like. The longitudinal position of the control rod 28, and ultimately the airfoil 26, can be adjusted with the control rod actuator 30. For instance, as illustrated in FIG. 3 the longitudinal position of the control rod 28 is such that the air foil 26 is displaced into a sealing engagement with the proximal end of the applicator tube 22.

Figure 2:
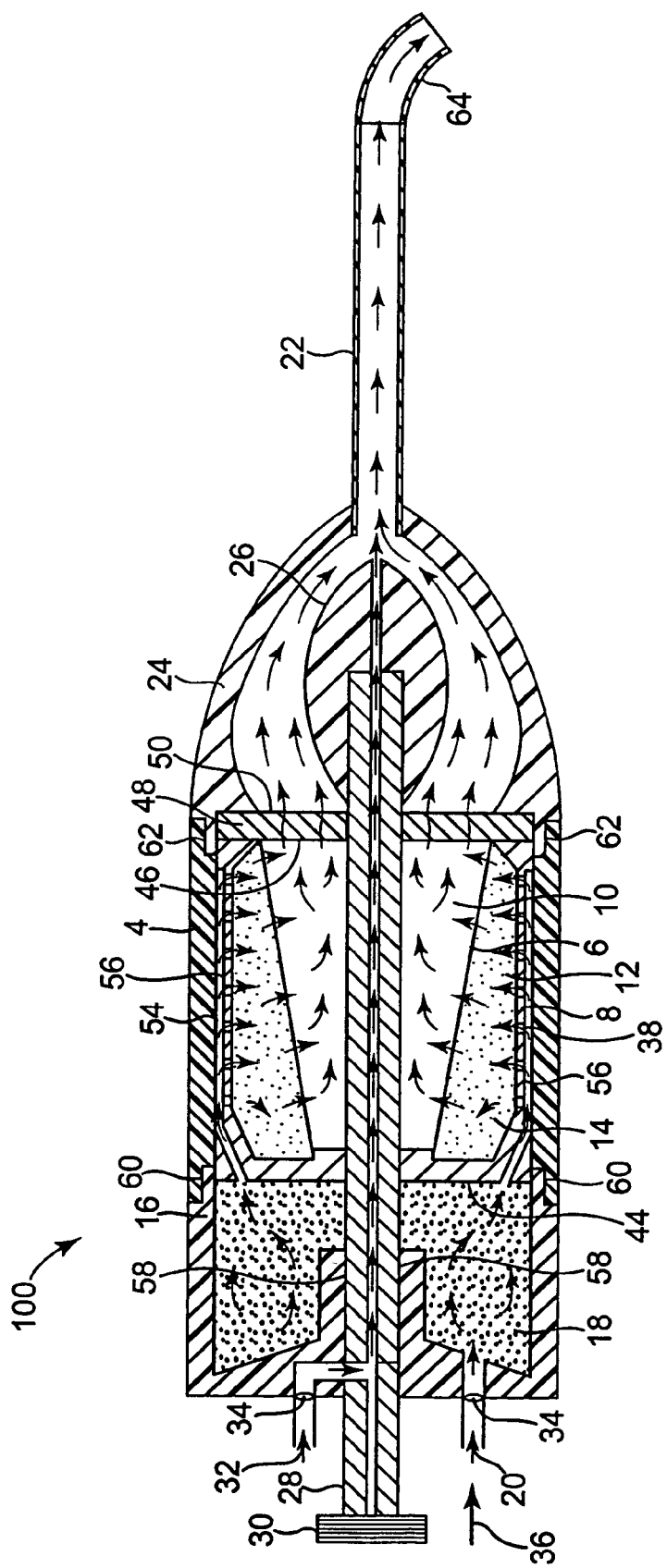
Figure 17:
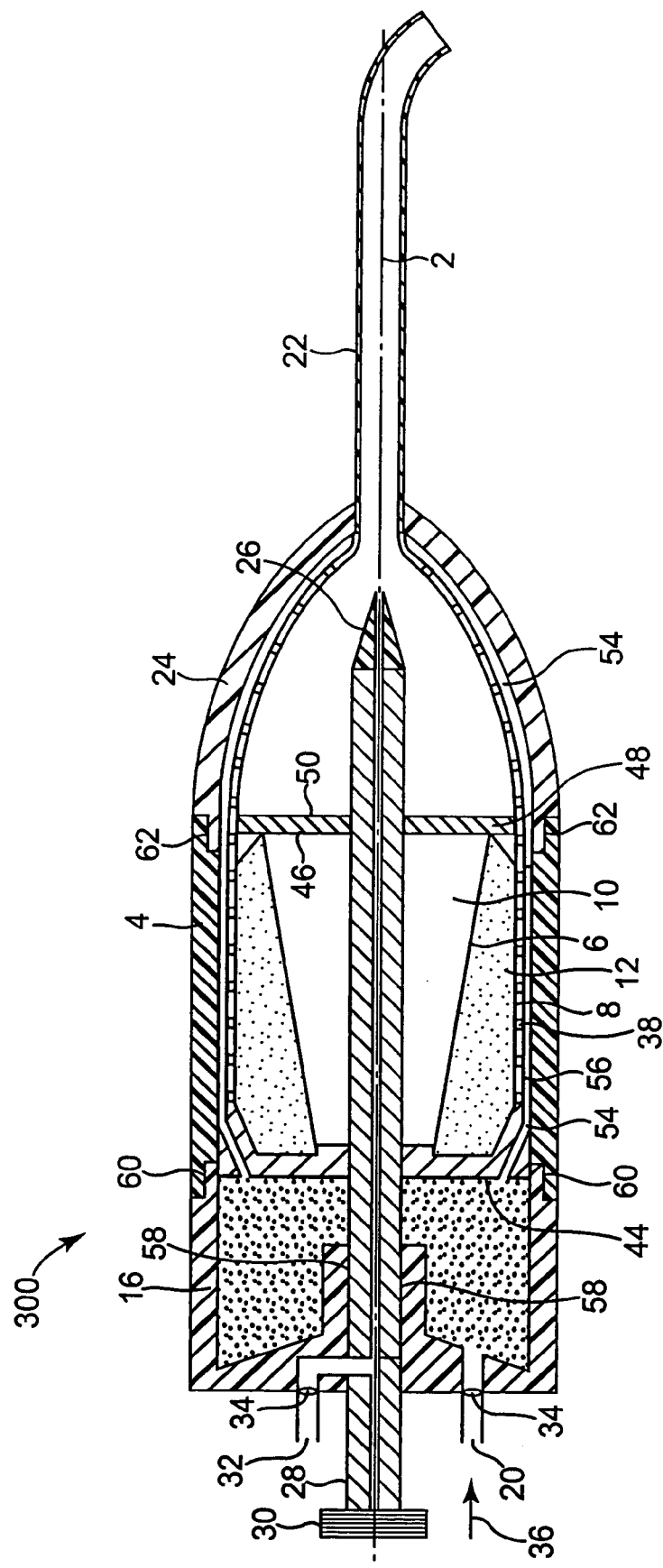
FIG. 17 is a schematic illustration in cross section parallel to the longitudinal axis of a dental powder applicator having an inner circumferential chamber to receive fluidized dental powder and an introductory circumferential chamber continuous from a desiccant chamber through an acceleration chamber in accordance with the present invention.

FIG. 2 illustrates the direction of airflow through a dental powder applicator 100 having an inner circumferential chamber 10 to receive fluidized dental powder 14. In this embodiment of the present invention, pressurized air enters the desiccant chamber 16 through a first air input opening 20 through a one-way valve. The pressurized air contacts the desiccant material 18 before flowing into the powder reservoir 4. The desiccated pressurized air flows through openings 38 located in the outer porous wall 8 and into the outer circumferential plenum chamber 12 containing the dental powder 14. In an alternative embodiment, as illustrated by FIG. 17, desiccated pressurized air flows through openings 38 located in the outer porous wall 8 which extends into the acceleration chamber. In one embodiment of the present invention, a membrane 56 is located within the introductory circumferential plenum chamber 54. The membrane 56 can reduce backflow of dental powder 14 from the powder reservoir 4 to the desiccant chamber 16. The dental powder 14 is fluidized around the entire perimeter of the outer porous wall 8 and travels with the pressurized air through the inner porous wall 6 towards the longitudinal axis 2 of the powder reservoir 4 and into the inner circumferential chamber 10. The inner circumferential chamber 10 is fluidly coupled to the acceleration chamber 24 and applicator tube 22. Thus, the desiccated pressurized air and dental material 13 travels from the inner circumferential chamber 10 into the acceleration chamber 24 passing the airfoil 26 to reach the applicator tube 22. The desiccated pressurized air and dental powder 14 then travels through the applicator tube 22, which can be directed, for instance, at a dental site.

Figure 4:
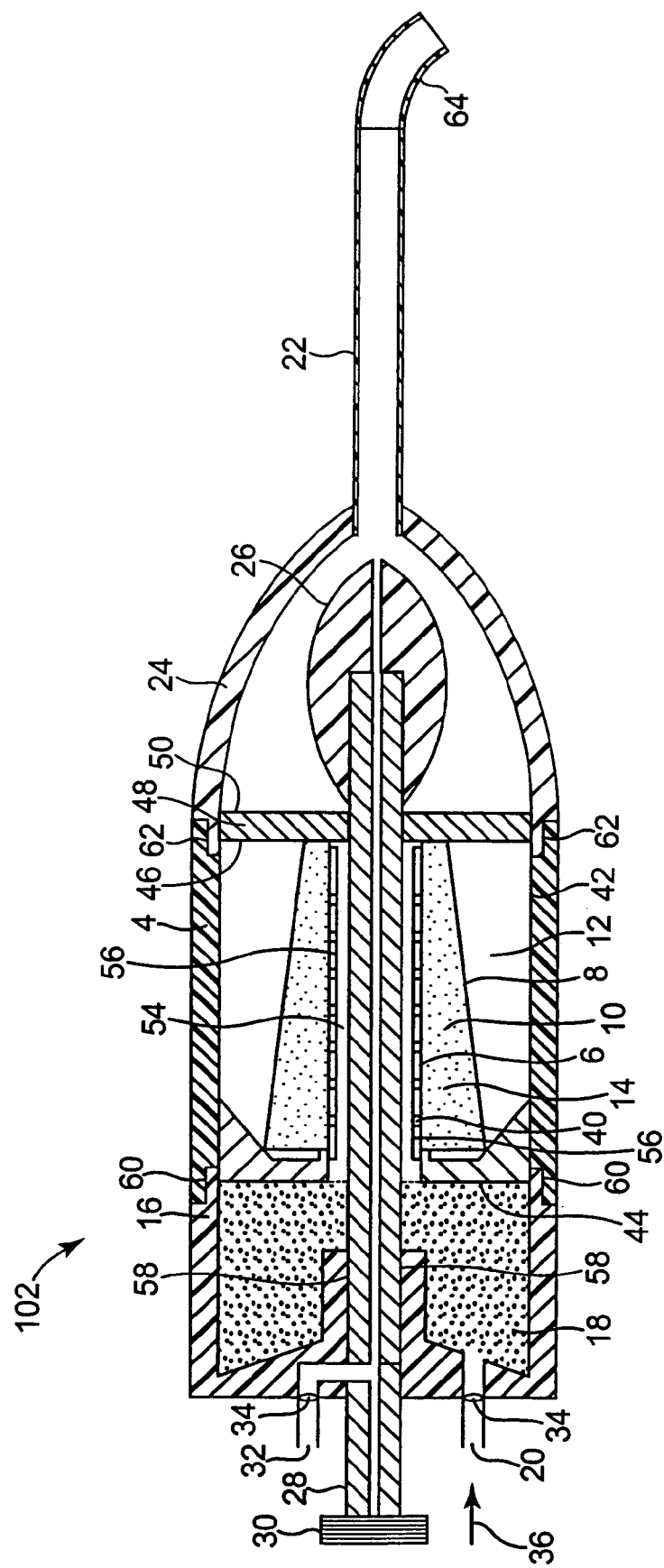
FIG. 4 is a schematic illustration in cross section parallel to the longitudinal axis of a dental powder applicator having an outer circumferential plenum chamber to receive fluidized dental powder in accordance with the present invention.
Figure 5:
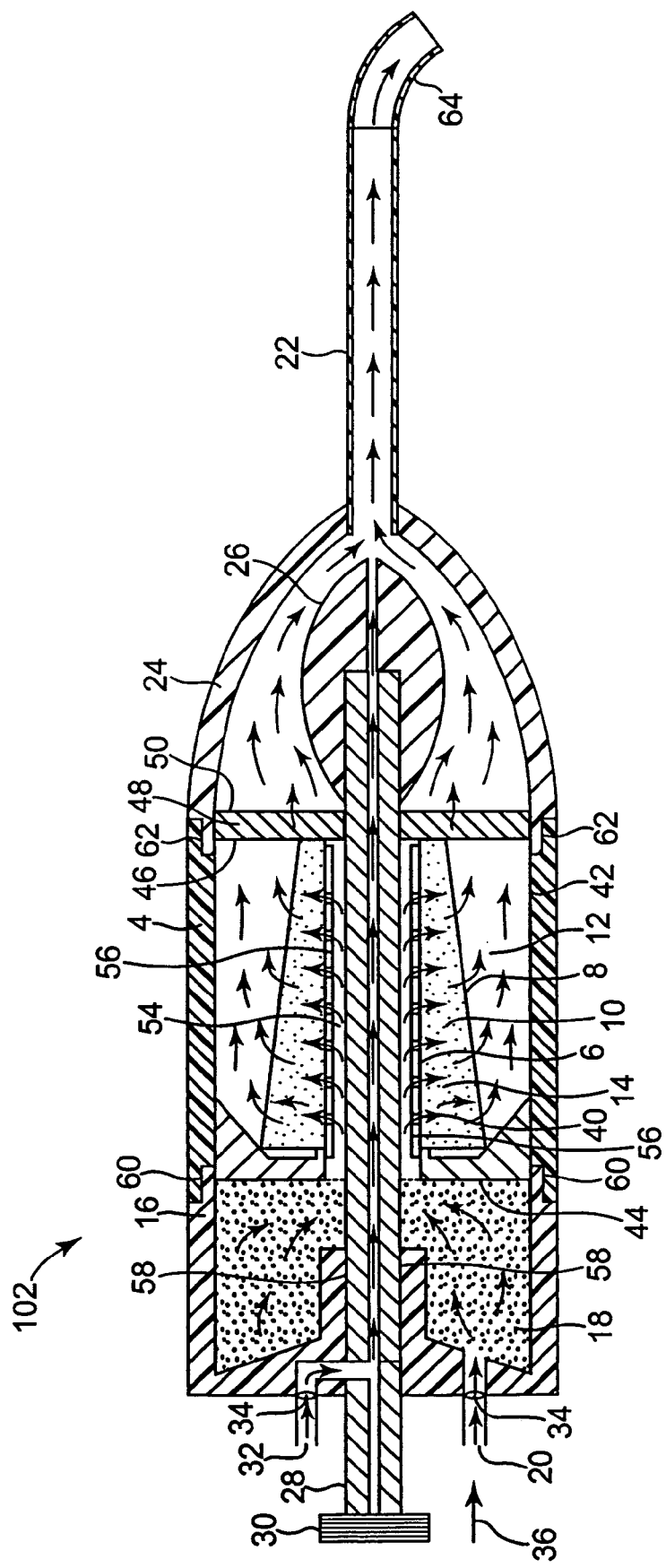
FIG. 5 is a schematic illustration in cross section parallel to the longitudinal axis of a dental powder applicator having an outer circumferential plenum chamber to receive fluidized dental powder showing the direction of air flow through the dental powder applicator in accordance with the present invention.
Figure 10:
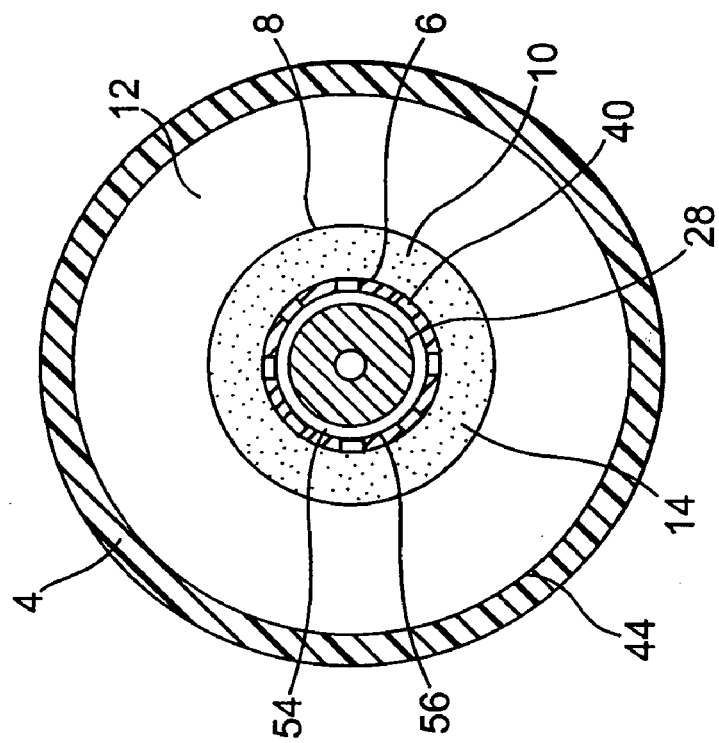
FIG. 10 is a schematic illustration of a cross sectional view perpendicular to the longitudinal axis of a powder reservoir having an outer circumferential plenum chamber to receive fluidized dental powder in accordance with the present invention.

Yet another embodiment of the present invention is illustrated by FIGS. 4 and 5. FIG. 4 is a schematic illustration of a cross sectional view of a dental powder applicator in accordance with the present invention having an outer circumferential plenum chamber 12 adapted to receive fluidized dental powder 14. The dental powder applicator 102 of FIG. 4 includes a powder reservoir 4 having an introductory circumferential plenum chamber 54 extending around a longitudinal axis 2 such that it is substantially surrounded by an inner circumferential chamber 10. The dental powder applicator also includes an inner porous wall 6 extending around the longitudinal axis 2 of the powder reservoir 4 and an outer porous wall 8 extending around the inner porous wall 6 and surrounding the inner circumferential chamber 10. In one embodiment of the present invention, a member 56 is located within the introductory circumferential plenum chamber 54 long the longitudinal axis 2 such that it substantially surrounds the inner porous wall 6. In an embodiment of the present invention, the membrane 56 can reduce backflow of dental powder 14 from the powder reservoir 4 to the desiccant chamber 16. The dental powder applicator 102 of the present invention further includes an outer circumferential plenum chamber 12 extending around the longitudinal axis 2 of the powder reservoir 4 and is substantially surrounded by an outer wall 42. In this embodiment, dental powder 14 is located in the inner circumferential chamber 10. FIG. 10 is a schematic illustration of a cross sectional view perpendicular to the longitudinal axis of a powder reservoir in accordance with the present invention having an outer circumferential plenum chamber 12 to receive fluidized dental powder 14.

This embodiment of the present invention also includes a desiccant chamber 16 containing a desiccant material 18 having a first end with a first air input opening 20 and a second air input opening 32 and a second end fluidly coupled to the introductory circumferential plenum chamber 54 of the powder reservoir 4. Also included is an applicator tube 22 having a proximal end fluidly coupled to the outer circumferential plenum chamber 12 and a distal end adapted to deliver the dental powder 14 to a dental site. In one embodiment of the present invention the desiccant chamber 16 can be joined to the powder reservoir 4 at a first coupling 60 by threads, sliding, pushing, snap connections, interference fits, spring connections and the like.

In this alternative embodiment of the present invention, the dental powder applicator 102 is further connected to a pressurized air source at a first air input opening 20 and a second air input opening 32 at a first end of the desiccant chamber 16. The pressurized air source can be, for example, compressed air. The pressurized air is directed into two distinct paths through one-way valves 34 that ensure unidirectional flow of the pressurized air. In one embodiment of the present invention, the pressurized air entering the first air input opening 20 is controlled with a variable flow switch that can be operated manually such as a foot pedal. Control of the pressurized air entering the second air input opening 32 opening is effected by an on/off switch such as a push button actuator or a variable fine control needle valve. In another embodiment control of the pressurized air entering the second air input opening is controlled by a control rod actuator 30. Pressurized air entering the first air input opening 20 is directed through the desiccant chamber 16 where it contacts the desiccant material 18. Pressurized air entering the second air input opening 32 is directed into a sealed chamber, prior to and separate from the desiccant chamber, and further flows from the sealed chamber into an interior portion 68 of a control rod 28.

The desiccated pressurized air is directed from the desiccant chamber 16 into the powder reservoir 4. In one embodiment, the desiccated pressurized air travels from the desiccant chamber 16 to the introductory circumferential plenum chamber 54 and then through a plurality of openings 38 located in the inner porous wall 6. In one embodiment, the openings 38 are generally cylindrical holes but other shapes that promote uniform and sufficient airflow are also contemplated by the present invention and are within the knowledge of one skilled in the art. The openings 38 have a maximum cross-sectional dimension of from about 50 microns to about 1-millimeter.

The openings 38 can be positioned in either a regular or irregular pattern in the outer porous wall 8 such that the openings 38 direct desiccated pressurized air into the powder reservoir 4 to substantially fluidize the dental powder in a random pattern. Because the openings 38 are positioned throughout the entire perimeter of the inner porous wall 6, desiccated, pressurized air enters the inner circumferential chamber 10 in a substantially 360-degree pattern. Thus, the dental powder applicator 102 can be oriented, tipped, held, rotated and the like in any direction and the dental powder 14 contained within the inner circumferential chamber 10 will still be agitated by the desiccated pressurized air and directed generally away from the longitudinal axis 2 of the powder reservoir 4.

The outer porous wall 8 of this embodiment separates the outer circumferential plenum chamber 12 from the inner circumferential chamber 10. The outer porous wall 8 of this embodiment of the present invention also includes openings 38. The openings 38 of the outer porous wall 8 have a maximum cross-sectional dimension of from about 50 microns to about 1-millimeter. The outer porous wall 8 can include one or more of a mesh screen, a membrane, a filter media, a perforated sheet material, or synthetic woven material. Thus, in one embodiment of the present invention, the outer porous wall 8 also filters particles of dental powder 14 that exceed the maximum cross-sectional dimension of the openings.

The dimensions of the outer porous wall 8 can also include a length measured in the direction of the longitudinal axis 2 that is from at least about two to about 10 times greater than a maximum gap between the inner porous wall 6 and the outer porous wall 8. As such, the present invention also provides uniform velocity of pressurized air along the entire length of the outer porous wall 8 as well as large as possible of an area for the fluidized particles to occupy in the powder reservoir 4. This further promotes, for example, a direct linear path of the fluidized dental powder 14 through the outer porous wall 8 to the outer circumferential plenum chamber 12 as well as sufficient surface area on the outer porous wall 8. The shape of the outer porous wall 8 of this embodiment can include, for example, a cylinder, a cone, or a continuously curved surface.

The present invention further includes an applicator tube 22 having a proximal end fluidly coupled to the outer circumferential plenum chamber 12 of the powder reservoir 4 and a distal end adapted to deliver the dental powder 14 to a dental site. In one embodiment of the present invention the applicator tube 22 is releasably attached to the dental powder applicator 102. In yet another embodiment, the applicator tube 22 is rotatably attached to the dental powder applicator 102. In one embodiment of the present invention a tip 64 can be joined to the distal end of the applicator tube 22. In one embodiment of the present invention the tip 64 is releasably attached. The tip 64 can also be adapted to deliver the dental powder 14 to a dental site. The tip 64 can be disposable or reusable. An example of a tip 64 is a disposable tip such as a Centrix ACCUDOSE high viscosity tube, (available from Centrix Dental, Shelton, Conn.).

Located generally between the powder reservoir 4 and the applicator tube 22 is an acceleration chamber 24. In one embodiment of the present invention, the powder reservoir 4 can be joined to the acceleration chamber 24 a second coupling 62 by threads, sliding, pushing, snap connections, interference fits, spring connections and the like.

Figure 7:
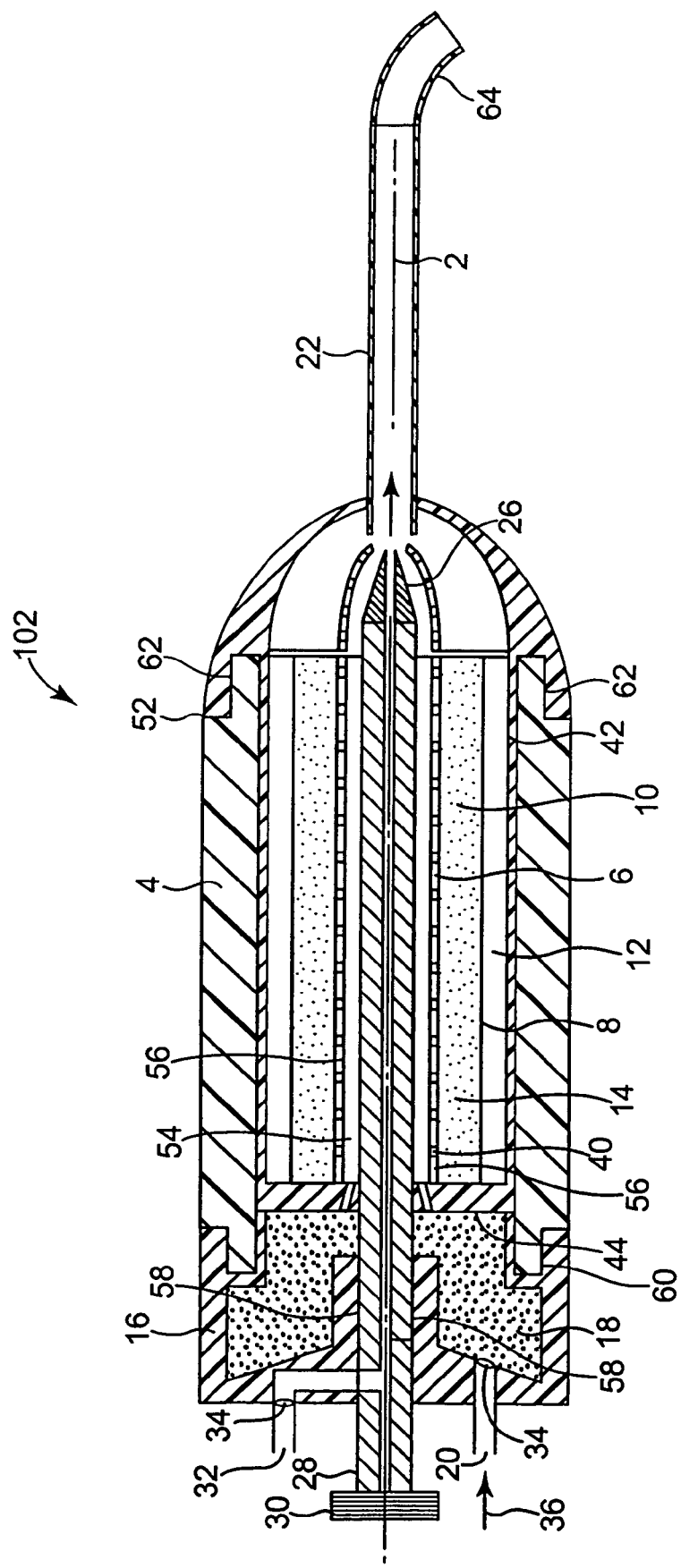
FIG. 7 is a schematic illustration of a cross section parallel to the longitudinal axis of a dental powder applicator having an outer circumferential plenum chamber to receive fluidized dental powder showing a powder chamber and an acceleration chamber as a combined assembly in accordance with the present invention.
Figure 8:
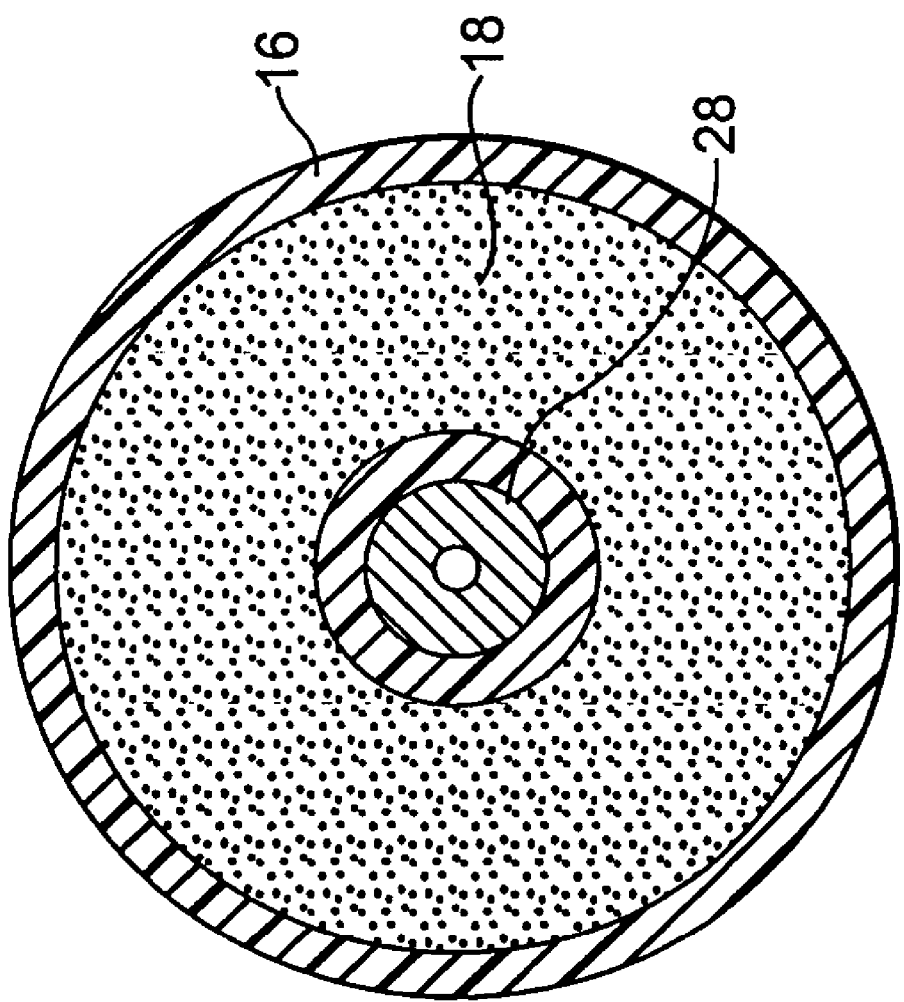
FIG. 8 is a schematic illustration of a cross sectional view perpendicular to the longitudinal axis of a desiccant chamber in accordance with the present invention.

In one embodiment of the present invention, the acceleration chamber 24 is fluidly coupled between the outer circumferential plenum chamber 12 of the powder reservoir 4 and the applicator tube 22. In one embodiment of the present invention, as illustrated in FIG. 7, the inner circumferential chamber 10 and acceleration chamber 24 are assembled as one piece. In this embodiment, the combined inner circumferential chamber 10 and acceleration chamber 24 can be connected to the cartridge onto the powder reservoir 4 and desiccant chamber 16. The cartridge can be pre-loaded with dental powder 14 and pressurized with a gas such as nitrogen to prevent ambient moisture in air from contaminating the dental powder 14 during periods of non-use.

The acceleration chamber 24 includes an airfoil 26 attached to the control rod 28. The fluidized dental powder 14 travels past the airfoil 26 to reach the distal end of the applicator tube 22. The shape and dimensions of the airfoil 26 also provide gradual acceleration of the fluidized dental powder 14 towards the proximal end of the applicator tube 22 with minimal disturbance or obstruction. As illustrated in FIGS. 16A–16D, suitable shapes for the airfoil 26 include fusiform, conical, tapered, and symmetrical shapes.

The acceleration chamber 24 includes an airfoil 26 coupled to the control rod 28 as is illustrated by FIG. 19. As is illustrated in FIGS. 16A–16D, in one embodiment of the present invention, the control rod 28 can be joined to the airfoil 26 at a third coupling 66 by threads, sliding, pushing, snap connections, interference fits, spring connections and the like. The fluidized dental powder 14 travels past the airfoil 26 to reach the distal end of the applicator tube 22. The airfoil 26 not only ensures a direct and straight path of flow for the fluidized dental powder 14 but the shape and dimensions of the airfoil 26 also provide gradual acceleration of the fluidized dental powder 14 towards the proximal end of the applicator tube 22 with minimal disturbance or obstruction.

As illustrated in FIGS. 16A–16D, suitable shapes for the airfoil 26 include fusiform, conical, tapered, and symmetrical shapes. The airfoil 26 is further connected to the control rod 28, which is adapted to, in part, displace the airfoil 26 within the acceleration chamber 24. More specifically, the control rod 28 includes a control rod actuator 30 to adjust the longitudinal position of the control rod 28, and ultimately the air foil 26, which affects the exit diameter of the opening to the proximal end of the applicator tube 22. Therefore, it is possible to regulate the volume and velocity of the fluidized dental powder 14 traveling through the acceleration chamber 24 and into the applicator tube 22. The airfoil 26 can also be displaced into a sealing engagement with the proximal end of the applicator tube 22, which can prevent ambient moisture in air from contaminating the dental powder 14 during periods of non-use. In one embodiment of the present invention, the control rod threaded 56 and is displaced by rotating the control rod actuator 30. Alternative methods of adjusting the longitudinal position of the control rod are also contemplated by the present invention however, such as by pushing and sliding the control rod in the longitudinal direction.

In another embodiment of the present invention, pressurized air entering the second air input opening 32 and flowing through the interior portion 68 of a control rod 28 can be used as supplemental pressurized air to further regulate the volume and velocity of the fluidized dental powder 14. The supplemental pressurized air can also provide a purging source or additional velocity of dental powder 14 free air to be directed through the applicator tube 22.

The control rod 28 of the present invention traverses the longitudinal axis 2 of the dental powder applicator 102 with the proximal end of the control rod 28 located at or near the first end of the desiccant chamber 16 and the distal end of the control rod 28 located within the acceleration chamber 24. As such, the control rod 28 extends through the desiccant chamber 16 and powder reservoir 4 and into an acceleration chamber 24. In one embodiment of the present invention, the control rod 28 extends out of the first end of the desiccant chamber 16. The control rod 28 is attached at a first or proximal end to the control rod actuator 30, which is further attached at a second or distal end to the airfoil 26. In one embodiment of the present invention, the control rod actuator 30 can be a knob, gripping device, handle or the like. The longitudinal position of the control rod 28, and ultimately the airfoil 26, can be adjusted with the control rod actuator 30. For instance, as illustrated in FIG. 3 the longitudinal position of the control rod 28 is such that the air foil 26 is displaced into a sealing engagement with the proximal end of the applicator tube 22.

FIG. 5 illustrates the direction of airflow through a dental powder applicator 102 having an outer circumferential plenum chamber 12 adapted to fluidized dental powder 14. In this embodiment of the present invention, pressurized air enters the desiccant chamber 16 through a first air input opening 20 through and on-way valve. The pressurized air contacts the desiccant material 18 before flowing into the powder reservoir 4. The desiccated, pressurized air flows through openings 38 located in the inner porous wall 6 and into the inner circumferential chamber 10 containing the dental powder 14. The dental powder 14 is fluidized around the entire perimeter of the inner porous wall 6 and travels with the desiccated pressurized air through the outer porous wall 8 away from the longitudinal axis 2 of the powder reservoir 4 and into the outer circumferential plenum chamber 12. The outer circumferential plenum chamber 12 is fluidly coupled to the acceleration chamber 24 and applicator tube 22. Thus, the desiccated pressurized air and dental powder 14 travel from the outer circumferential plenum chamber 12 into the acceleration chamber 24 passing the airfoil 26 to reach the applicator tube 22. The desiccated pressurized air and dental powder 14 then travel through the applicator tube 22, which can be directed, for instance, at a dental site.

In one embodiment of the present invention, as is depicted in FIG. 12, the dental powder applicator 100 includes a series of elements. Specifically, FIG. 12 is a schematic illustration of a cross sectional view of a dental powder applicator in accordance with the present invention showing the arrangement of the component parts. Starting at a first end of the dental powder applicator 100 is the desiccant chamber 16. Proceeding in the longitudinal direction of the dental powder applicator 100, the next element is a first o-ring 44 located proximate a second end of the desiccant chamber 16 and between the second end of the desiccant chamber 16 and a first end of the powder reservoir 4. A second o-ring 46 is located between a second end of the powder reservoir 4 and a first end of a powder reservoir end cap 48. The powder reservoir end cap 48 provides, for example, a seal for the powder reservoir 4 as well as support for the control rod 28. The powder reservoir end cap 48 can further be integral to the powder chamber or a separate piece. A third o-ring 50 is located between a second end of the powder reservoir end cap 48 and a first end of the acceleration chamber 24. Next is the applicator tube 22, which is connected at a proximal end to the second end of the acceleration chamber 24. Pressurized air enters the first end of the desiccant chamber. Dental powder 14 propelled by the desiccated pressurized air thus exits at the distal end of the applicator tube 22.

The desiccant chamber 16 of the present invention houses, for example, the desiccant material 18 as well as the proximal end of the control rod 28. The desiccant chamber 16 further includes the first air input opening 20 and second air input opening 32 for the dental powder applicator 100. Suitable materials of construction for the desiccant chamber 16 include, for example, aluminum, stainless steel, rigid PVC materials, polytetrafluoroethylene available as TEFLON® from DuPont, acetal polyoxymethylene available as DELRIN® from DuPont and titanium.

Another element of the present invention is the powder reservoir 4. In one embodiment of the present invention, the powder reservoir 4 houses, for example, the introductory circumferential plenum chamber 54, the membrane 56, the inner porous wall 6, the outer porous wall 8, the inner circumferential chamber 10 and the outer circumferential plenum chamber 12. The control rod 28 traverses the powder reservoir 4 along the longitudinal axis 2 of the powder reservoir 4 and is surrounded generally by the inner circumferential chamber 10. The dental powder 14 is also housed within the powder reservoir 4. In one embodiment of the present invention, the dental powder is located in between the inner porous wall 6 and the outer porous wall 8 such that the dental powder is located in the outer circumferential plenum chamber 12 of the dental powder applicator 100 of FIG. 1. Alternatively, the dental powder can be located in the inner circumferential chamber 10 of the powder reservoir 4 as is illustrated in the dental powder applicator 102 of FIG. 4. Suitable materials of construction for the desiccant chamber 16 include, for example, aluminum, stainless steel, rigid PVC materials, polytetrafluoroethylene available as TEFLON® from DuPont, acetal polyoxymethylene available as DELRIN® from DuPont and titanium.

Elements of the powder reservoir 4 are designed to be replaceable or alternatively, refillable. For example, in one embodiment of the present invention, the inner porous wall 6 and outer circumferential plenum chamber 11 and outer porous wall 8 provide a cartridge that can be removed from the powder reservoir 4 and replaced with a new cartridge containing a dental powder, for instance, or refilled with dental powder. In an alternative embodiment, the outer porous wall 8, inner circumferential chamber 10 and inner porous wall 6 are the elements that provide the replaceable and removable cartridge. In one embodiment of the present invention, a cartridge loaded with fresh dental powder 14 is simply replaced when an existing cartridge in the powder reservoir is replete of dental powder 14. The design of the present invention makes it possible to continue using the existing cartridge, however, even at low levels of dental powder 14. FIGS. 18A, 18B and 21 illustrate replaceable or refillable cartridges.

The acceleration chamber 24 of the present invention houses, for example, the air foil 26 as well as the distal end of the control rod 28. The dimensions of the acceleration chamber 24 can be altered by changing the position of the airfoil 26 using the control rod actuator 30. In FIG. 3, for example, the airfoil 26 is in a sealing engagement with the applicator tube 22. Suitable materials of construction for the acceleration chamber 24 include, for example, aluminum, stainless steel, rigid PVC materials, polytetrafluoroethylene available as TEFLON® from DuPont, acetal polyoxymethylene available as DELRIN® from DuPont and titanium.

The applicator tube 22 of the present invention is releasably attached at a proximal end to the second end of the acceleration chamber 24. The applicator tube 22 further rotates a full 360 degrees to provide full range of use during application of dental powder 14 to the dental site. The applicator tube can be constructed of, for example, material rigid enough to be able to force objects, such as the cheek of a patient, away from the area surrounding the dental site and thus permitting full access. Accordingly, suitable materials of construction for the acceleration chamber 24 include, for example, stainless steel and titanium.

Because the applicator tube 22 and/or tip 64 can be released from the dental powder applicator 100 of the present invention, it is possible to use the same dental powder applicator and/or tip 64 with multiple patients by simply removing the used applicator tube 22 and/or tip 64 and attaching an unused applicator tube 22 and/or tip 64.

As previously described, the present invention includes a desiccant material 18 located within the desiccant chamber 16. As pressurized airflow is directed through the desiccant chamber 16 it comes in contact with the desiccant material 18. The desiccant material 18 absorbs moisture out of the pressurized air resulting in desiccated pressurized air that can be introduced into the powder reservoir 4. The removal of the moisture from the pressurized air reduces the potential for clumping of the dental powder 14. Suitable desiccant materials 17 include, for example, activated alumina, silica gel desiccants, clay absorbents and mixtures thereof.

The dental powder applicator 100 of the present invention can be used to deposit dental powder 14 to a dental site. In one embodiment of the present invention, the dental powder is used to enhance the imaging process during restorative dental procedures. As such, the dental powder is generally selected based on its ability to contribute directly to an improvement in image contrast by affecting the signal intensity emanating from the dental site coated with the dental powder. The dental powder can also be referred to as a contrast medium or reflective powder and includes pharmaceutically safe powders such as titanium dioxide.

In yet another embodiment of the present invention is a method of delivering dental powder 14 to a dental site. Delivery of the dental powder 14 includes the steps of introducing pressurized air into a desiccant chamber 16 of an orientation independent dental powder applicator 100 (also referred to as a dental powder applicator), such as the dental powder applicator 100 previously described, through a first air input opening 20 and desiccating the pressurized air. The method further includes the steps of directing the desiccated pressurized air into a powder reservoir 4 and then circumferentially fluidizing the dental powder 14 contained in the powder reservoir 4 with the desiccated pressurized air. The fluidized dental powder 14 and desiccated pressurized air is then directed towards an applicator tube 22 along a longitudinal axis 2 of the dental powder applicator 100. The fluidized dental powder 14 and desiccated pressurized air is additionally directed through the applicator tube 22, the applicator tube 22 having a distal end directed towards the dental site. The distal end of the applicator tube 22 can be directed towards the dental site, for example, by rotating the applicator tube 22 to direct the dental powder 14 onto the dental site. Further, the dental powder applicator 100 itself can be positioned at any angle to provide full access to the dental site.

In another embodiment of the present invention the method of delivering dental powder 14 to a dental site includes the step of connecting the orientation independent dental powder applicator 100 to a pressurized air source 36 at a first end of the desiccant chamber 16. In yet another embodiment, delivery of the dental powder 14 can be controlled, for example, using a pressurized air manual switch, such as a foot peddle, or a control rod actuator 30. Additionally, the delivery of dental material 14 can be controlled using supplemental pressurized air. In this embodiment, the method includes the step of introducing pressurized air into a second air input opening 32 that is fluidly coupled to a control rod 28, the control rod 28 having a fluid path adapted to deliver the supplemental pressurized air. In a further embodiment of the present invention the method includes the step of directing the fluidized dental powder 14 and desiccated pressurized air through an acceleration chamber 24, the acceleration chamber 24 having an air foil 26 adapted to promote continuous flow and gradual acceleration of the fluidized dental powder 24 and desiccated pressurized air. The acceleration further promotes a direct, straight flow path of the fluidized dental powder 14 and desiccated pressurized air along the longitudinal axis of the dental powder applicator 100.

Following application of the dental powder 14, the applicator tube 22 and/or tip 64 can be released from the dental powder applicator 100. The applicator tube 22 and/or tip 64 can then be discarded or sanitized for future use. Following this procedure, the applicator tube 22 can be reattached to the dental powder applicator 100. Similarly, the powder reservoir 4 of the present invention can be replaced or refilled. Thus, in one embodiment of the present invention is a method of replacing the powder reservoir 4 with a new cartridge of dental powder 14.

Figure 22:
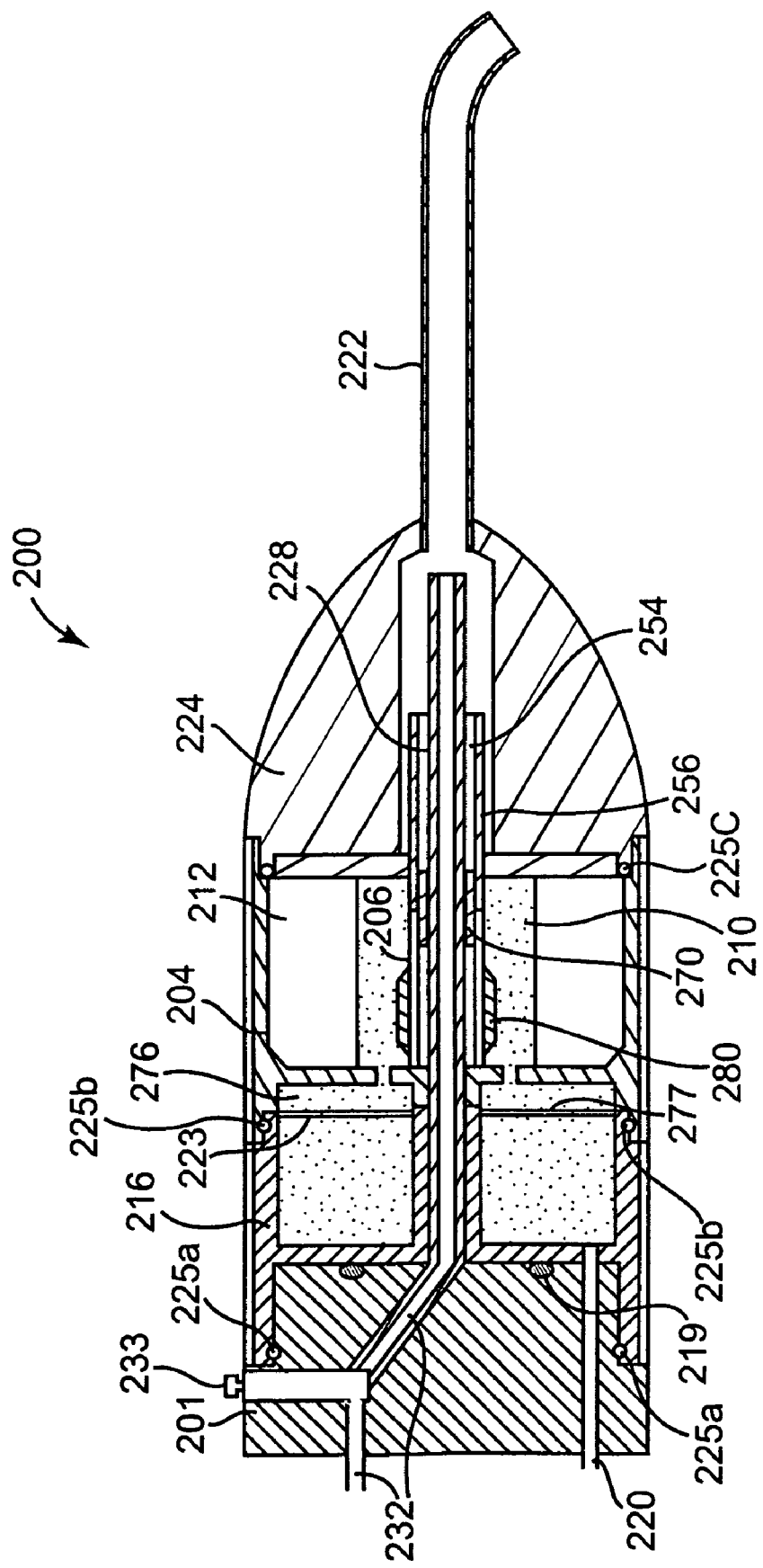
FIG. 22 is a schematic illustration in cross section parallel to the longitudinal axis of a dental powder applicator having a desiccant cartridge in accordance with an embodiment of the present invention.

FIG. 22 is a schematic illustration of a cross sectional view of a dental powder applicator 200 in accordance with another embodiment of the present invention. Moving from a proximal direction to a distal direction, or from left to right in the FIG. 22, the dental power applicator 200 includes a base 201, a desiccant chamber 216, a powder reservoir 204, an acceleration chamber 224 and an applicator tube 222. A control rod 228 extends through the powder reservoir 204 and is in fluid communication with the base 201 and the applicator tip 210.

The base 201 is adapted for connection with a source of pressurized air. The base 201 includes a first input flow 220 that is in fluid communication with the desiccant chamber 216 and the powder reservoir 204. The air flowing through the first input flow 220 acts to fluidize or aerate dental powder contained in the powder reservoir 204. The flow of pressurized air through the first input flow 220 is controlled with a variable flow switch that can be operated manually, such as a foot pedal. The base 201 includes a second input flow 232 directed through the control rod 228. The flow of air through the second input flow 232 is controlled with an actuator 233 located on the base 201. The actuator 233 is positioned to be actuatable by the operator with the same hand that is maneuvering the dental powder applicator 200. The dental powder applicator 200 is thus a one-handed device, in which the operator's other hand is left free.

Figure 23:
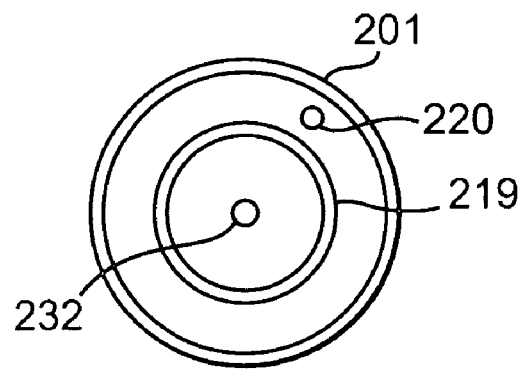
FIG. 23 is an end view of the base of the dental powder applicator of FIG. 22.

In one embodiment, as is shown in FIG. 23, the base 201 includes an o-ring seal 219 disposed on a distal face 221 of the base 201. The seal 219 is disposed around the second input flow 232 and between the second input flow 232 and the first input flow 220. The seal 219 functions to seal the base 201 to the desiccant chamber 216 and takes the place of the one-way valves discussed with respect to previous embodiments. The seal 219 further seals the second input flow 232 from the first input flow 220. The dental powder applicator 200 may include additional seals for sealing various components to one another. In one embodiment, as is shown in FIG. 22, the dental powder applicator 200 includes an o-ring seal 225a between the dessicant chamber 216 and the base 201, an o-ring seal 225b between the between the dessicant chamber 216 and the powder reservoir 204, and an o-ring seal 225c between the acceleration chamber 224 and the powder reservoir 204. Other seals may be provided as necessary to prevent leaks of dental powder and/or dessicant material from the dental powder applicator 200, and to isolate the first input flow 220 from the second input flow 232.

As is shown in FIG. 22, air flows through the first input flow 220 into the desiccant chamber 216, which holds desiccant material. The distal end of the desiccant chamber 216 is covered by a porous member 223 that retains the desiccant material within the desiccant chamber 216 but permits air to flow distally. The desiccant chamber 216 is releasably attached to both the base 201 and the powder reservoir 204. In the present embodiment, the desiccant chamber 216 is in the form of a cartridge and may be 216 is threadedly engaged to the base 201 and to the powder reservoir 204. When the desiccant chamber 216 is tightly threaded to the base 201, the second input flow 232 is sealed from the dental powder material contained in the powder reservoir 204. However, the desiccant chamber 216 may be releasably attached to the base 201 and powder reservoir 204 through a snap fit, locking pin, or any combination of the like adapted to seal the second input flow 232 from the dental powder reservoir 204.

The powder reservoir 204 is configured generally similarly to the powder reservoirs described in previous embodiments. In this particular embodiment, the powder reservoir 204 extends about a longitudinal axis 2. The powder reservoir 204 includes an inner porous wall 206 that surrounds an introductory circumferential plenum chamber 254 of the powder reservoir 204. The powder reservoir 204 further includes an outer porous wall 208 extending around and substantially surrounding the inner porous wall 206. The area located between the outer porous wall 208 and the inner porous wall 206 is an inner circumferential chamber 210. The inner circumferential chamber 210 extends around the longitudinal axis 2 of at least the inner porous wall 206. The powder reservoir 204 also includes an outer circumferential plenum chamber 212 extending around the longitudinal axis 2 and surrounding the outer porous wall 208.

In the present embodiment, the powder reservoir 204 is releasably attached to the desiccant chamber 216, as described above, as well as to the acceleration chamber 224. The powder reservoir 204 may take the form of a cartridge and may be removable, refillable, reusable or disposable. In one embodiment, the powder reservoir 204 is threadedly engaged to the acceleration chamber 224. However, the powder reservoir 204 may be releasably attached to the acceleration chamber 224 through a screw fit, locking pin, or any combination of the like.

As is shown in FIG. 22, the powder reservoir 204 further includes a membrane or perforated tube 256 extending around the longitudinal axis 2 and substantially surrounded by the inner circumferential chamber 210. The membrane 256 can reduce backflow of dental powder from the powder reservoir 204 to the desiccant chamber 216. The membrane 256 extends into the acceleration chamber 224 and provides increased control over the direction of the flow of fluidized dental powder through the applicator tube 222. The control rod 228 is surrounded by the membrane 256 and also extends into the acceleration chamber 224 for controlling the flow of fluidized dental powder into the applicator tube 222.

Figure 24:
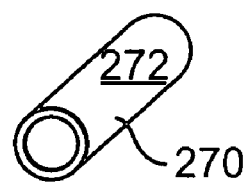
FIG. 24 is a perspective view of the agitator member of the dental powder applicator of FIG. 22.
Figure 25:
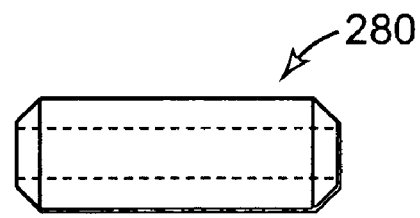
FIG. 25 is a perspective view of the movable auxiliary desiccant chamber of the dental powder applicator of FIG. 22.

In one embodiment, the dental power applicator 200 further includes at least a first agitator member 270. Upon agitation or shaking of the dental powder applicator 200, the agitator member 270 moves within the dental powder applicator 200, breaking up clumps of dental powder or foreign objects. In one embodiment, as is shown in FIGS. 22 and 24, the agitator member 270 is a hollow tube slidably disposed within the introductory circumferential plenum chamber 254. The agitator member 270 is sized relative to the membrane 256 such that an outer surface 272 of the agitator member 270 is in close proximity to an inner surface 274 of the membrane 256. Thus, when the agitator member 270 slides within the introductory circumferential plenum chamber 254 upon agitation of the dental powder applicator 200, the agitator member 270 shears off any clumps of dental powder, desiccant or any other foreign material that may have formed on the inner surface 274 of the membrane 256.

In other embodiments, the agitator member 270 is disposed elsewhere within the dental powder applicator 200 and may take on other configurations. The agitator member 270 may be slidably or movably engaged with other components of the dental powder applicator 200, or may be disposed loose within, for example, the inner circumferential chamber 210 containing the dental powder, in a manner similar to that commonly found in bottles of nail polish. In this manner, clumps of dental powder or foreign material may be broken up without disassembling the dental powder applicator 200.

In one embodiment, as is shown in FIG. 22, the dental powder applicator 200 further includes an auxiliary desiccant chamber 276 containing desiccant material. The auxiliary desiccant chamber 276 provides further desiccation of the dental powder after the pressurized air has passed through the desiccant chamber 216. The auxiliary desiccant chamber 276 may be fixed to a component of the dental powder applicator 200, for example, a proximal end of the powder reservoir 204. In this embodiment, the auxiliary desiccant chamber 276 is covered by a porous member 277 which permits air to flow in from the desiccant chamber 216. The auxiliary desiccant chamber 276 may be permanently attached to the dental powder applicator 200, or may be removably or releasably attached to the dental powder applicator 200 such that the auxiliary desiccant chamber 276 may be replaced or refilled.

In other embodiments, the dental powder applicator 200 further includes an auxiliary desiccant chamber 280 containing desiccant material that is movably disposed within the dental powder applicator 200. As is shown in FIGS. 22 and 26, the auxiliary desiccant chamber 280 is positioned within the inner circumferential chamber 210 and is slidably disposed about the membrane 256. In this embodiment, the auxiliary desiccant chamber 280 also functions as an agitator member. Upon agitation of the dental powder applicator 200, the auxiliary desiccant chamber 280 slides over the membrane 256 within the inner circumferential chamber 210, breaking up clumps of dental powder. In other embodiments, the auxiliary desiccant chamber 280 is movably disposed elsewhere, for example, about the inner porous wall 206, about the outer porous wall 208 or within the outer circumferential plenum chamber 212.

Although the present invention has been described with reference to preferred embodiments, workers skilled in the art will recognize that changes may be made in form and detail without departing from the spirit and scope of the invention. In addition, the invention is not to be taken as limited to all of the details thereof as modifications and variations thereof may be made without departing from the spirit or scope of the invention.

What is claimed is:

1. An orientation independent dental powder applicator comprising:
    a powder reservoir having an introductory circumferential plenum chamber extending around a longitudinal axis;
    an inner porous wall extending around the longitudinal axis and substantially surrounding the introductory circumferential plenum chamber;
    an outer porous wall extending around the inner porous wall and substantially surrounding an inner circumferential chamber;
    an outer circumferential plenum chamber extending around the longitudinal axis and substantially surrounded by an outer wall;
    a dental powder located in the inner circumferential chamber; and
    a desiccant chamber containing a desiccant material having a first end with a first air input opening and a second end fluidly coupled to the introductory circumferential plenum chamber, wherein the desiccant chamber is releasably attached to the powder reservoir.

2. The dental powder applicator of claim 1 further comprising a base adapted for coupling to a source of pressurized air and to the air input opening, wherein the desiccant chamber is releasably attached to the base.

3. The dental powder applicator of claim 2 further comprising a seal member between the base and the desiccant chamber.

4. The dental powder applicator of claim 1 further comprising:
    an applicator tube comprising a proximal end fluidly coupled to the outer circumferential plenum chamber and a distal end adapted to deliver the dental powder to a dental site;
    a control rod having a first end in fluid communication with a source of pressurized air and a second end in fluid communication with the applicator tube; and
    an actuator disposed on the dental powder applicator for controlling the flow of air through the control rod.

5. The dental powder applicator of claim 1 further comprising an auxiliary desiccant chamber containing a desiccant material releasably attached to the powder reservoir.

6. The dental powder applicator of claim 1 further comprising an auxiliary desiccant chamber is movably disposed within the powder reservoir.

7. The dental powder applicator of claim 1 further comprising an agitator member movably disposed within the powder reservoir.

8. The dental powder applicator of claim 7 wherein the agitator member further comprises an auxiliary desiccant chamber containing a desiccant material.

9. The dental powder applicator of claim 7 wherein the powder reservoir further comprises a perforated tube extending around the longitudinal axis and substantially surrounded by the inner circumferential chamber, wherein the agitator member is slidably engageable within the perforated tube.

10. An orientation independent dental powder applicator of the type including a powder reservoir having an introductory circumferential plenum chamber extending around a longitudinal axis, an inner porous wall extending around the longitudinal axis and substantially surrounding the introductory circumferential plenum chamber, an outer porous wall extending around the inner porous wall and substantially surrounding an inner circumferential chamber, an outer circumferential plenum chamber extending around the longitudinal axis and substantially surrounded by an outer wall, and a dental powder located in the inner circumferential chamber, wherein the dental powder applicator comprises:

a desiccant chamber containing a desiccant material having a first end with a first air input opening and a second end fluidly couplable to the introductory circumferential plenum chamber, wherein the desiccant chamber is releasably attachable to the powder reservoir.

11. The dental powder applicator of claim 10 wherein the desiccant chamber is releasably couplable to a source of pressurized air.

12. The dental powder applicator of claim 10 wherein the desiccant chamber is adapted to be disposable.

13. The dental powder applicator of claim 10 wherein the desiccant chamber is adapted to be refillable.

14. A method of delivering dental powder to a dental site comprising the steps of:

introducing pressurized air into a desiccant chamber of an orientation independent dental powder applicator through a first air input opening;

desiccating the pressurized air;

directing the desiccated pressurized air into a powder reservoir;

circumferentially fluidizing the dental powder contained in the powder reservoir with the desiccated pressurized air;

directing the fluidized dental powder and desiccated pressurized air towards a dental site; and replacing the desiccant material when it becomes depleted.

15. The method of claim 14 wherein replacing the desiccant material includes replacing the desiccant chamber with a new cartridge of desiccant material.

16. The method of claim 14 wherein replacing the desiccant material includes refilling the desiccant chamber with a new cartridge of desiccant material.

17. The method of claim 14 further comprising the step of agitating an agitator member within the powder reservoir to break up material within the powder reservoir.

18. The method of claim 14 further comprising desiccating the fluidized dental powder.

19. The method of claim 14 wherein introducing the pressurized air includes operating an actuator disposed on the dental powder applicator.

20. The method of claim 19 wherein the actuator is disposed on the dental powder applicator so as to be operable by the same hand as is directing the fluidized dental powder and desiccated pressurized air towards the dental site.

* * * * *